(12) United States Patent
Kitamura et al.

(10) Patent No.: US 11,578,112 B2
(45) Date of Patent: Feb. 14, 2023

(54) LONG-ACTING ADRENOMEDULLIN DERIVATIVE CONJUGATED WITH FC REGION OF IMMUNOGLOBULIN

(71) Applicant: UNIVERSITY OF MIYAZAKI, Miyazaki (JP)

(72) Inventors: Kazuo Kitamura, Miyazaki (JP); Motoo Yamasaki, Miyazaki (JP); Sayaka Nagata, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 0 days.

(21) Appl. No.: 16/498,086

(22) PCT Filed: Mar. 29, 2018

(86) PCT No.: PCT/JP2018/013075
§ 371 (c)(1),
(2) Date: Sep. 26, 2019

(87) PCT Pub. No.: WO2018/181638
PCT Pub. Date: Oct. 4, 2018

(65) Prior Publication Data
US 2021/0115103 A1 Apr. 22, 2021

(30) Foreign Application Priority Data
Mar. 29, 2017 (JP) .............................. JP2017-064369

(51) Int. Cl.
*C12N 15/62* (2006.01)
*C07K 14/575* (2006.01)
*C12P 21/02* (2006.01)
*A61K 38/00* (2006.01)

(52) U.S. Cl.
CPC ............ *C07K 14/575* (2013.01); *C12N 15/62* (2013.01); *C12P 21/02* (2013.01); *A61K 38/00* (2013.01)

(58) Field of Classification Search
CPC .................................................. C12N 16/52
See application file for complete search history.

(56) References Cited

U.S. PATENT DOCUMENTS

| 5,639,855 A | 6/1997 | Kitamura et al. |
| 2009/0252703 A1 | 10/2009 | Gegg, Jr. et al. |
| 2013/0296260 A1 | 11/2013 | Kitamura et al. |

FOREIGN PATENT DOCUMENTS

| CN | 106164088 A | 11/2016 |
| EP | 3 127 914 A1 | 2/2017 |
| JP | 07-196693 A | 8/1995 |
| JP | 2774769 B2 | 4/1998 |
| JP | 4830093 B | 10/2006 |
| WO | WO 2007/018619 A2 | 2/2007 |
| WO | WO 2012/096411 A1 | 7/2012 |
| WO | WO 2012/138867 A2 | 10/2012 |
| WO | WO 2013/009539 A1 | 1/2013 |
| WO | WO 2013/064508 A1 | 5/2013 |
| WO | WO 2016/014428 A2 | 1/2016 |
| WO | WO 2016/046301 A1 | 3/2016 |

OTHER PUBLICATIONS

Kitamura et al, The Intermediate Form of Glycine-Extended Adrenomedullin Is the Major Circulating Molecular Form in Human Plasma. Biochemicaland Biophysical Research Communications 244, 551-555 (1998).*
Chen et al, Fusion protein linkers: Property, design and functionality. Advanced Drug Delivery Reviews 65 (2013) 1357-1369.*
Kitamura et al, Adrenomedullin: A Novel Hypotensive Peptide Isolated from Human Pheochromocytoma. Biochemical and Biophysical Research Communications vol. 192, Issue 2, Apr. 30, 1993, pp. 553-560.*
Belloni et al., "Structure-Activity Relationships of Adrenomedullin in the Adrenal Gland," Endocrine Research, 1998, 24(3&4):729-730.
Champion et al., "Catecholamine Release Mediates Pressor Effects of Adrenomedullin-(15-22) in the Rat," Hypertension, Nov. 1996, 28(5):1041-1046.
Champion et al., "Structure-activity relationships of adrenomedullin in the circulation and adrenal gland," Regulatory Peptides, 1999, 85:1-8.
Eguchi et al., "Structure-Activity Relationship of Adrenomedullin, a Novel Vasodilatory Peptide, in Cultured Rat Vascular Smooth Muscle Cells," Endocrinology, 1994, 135(6):2454-2458.
Garcia et al., "Synthesis, Biological Evaluation, and Three-Dimensional Quantitative Structure-Activity Relationship Study of Small-Molecule Positive Modulators of Adrenomedullin," J. Med. Chem., 2005, 48:4068-4075.
Kato et al., "Bench-to-bedside pharmacology of adrenomedullin," European Journal of Pharmacology, 2015, 764:140-148.
Kitamura et al., "Adrenomedullin: A Novel Hypotensive Peptide Isolated from Human Pheochromocytoma," Biochemical and Biophysical Research Communications, Apr. 30, 1993, 192(2):553-560.
Kubo et al., "Biological properties of adrenomedullin conjugated with polyethylene glycol," Peptides, 2014, 57:118-121.
Mitsuda et al., "Large-scale production of functional human adrenomedullin: expression, cleavage, amidation, and purification," Protein Expression and Purification, 2002, 25:448-455.

(Continued)

*Primary Examiner* — Tekchand Saidha
(74) *Attorney, Agent, or Firm* — Morgan, Lewis & Bockius LLP

(57) ABSTRACT

The invention provides a novel adrenomedullin derivative sustainable for a long period which is capable of substantially suppressing unwanted side effects while maintaining pharmacological effects of adrenomedullin. An aspect of the invention relates to a compound represented by formula (I): [wherein A is an Fc region of an immunoglobulin, B is a peptide moiety derived from adrenomedullin or a modified form thereof with adrenomedullin activity, and L is a linking group comprising a peptide having any given amino acid sequence] or a salt thereof, or a hydrate thereof. Another aspect of the invention relates to a method for producing the compound represented by formula (I), and a medicament comprising the compound as an active ingredient.

A-L-B (I).

10 Claims, 5 Drawing Sheets

Specification includes a Sequence Listing.

(56) References Cited

OTHER PUBLICATIONS

Roldos et al., "Small-Molecule Negative Modulators of Adrenomedullin: Design, Synthesis, and 3D-QSAR Study," ChemMedChem, 2008, 3(9):1345-1355.

Watanabe et al., "Vasopressor Activities of N-Terminal Fragments of Adrenomedullin in Anesthetized Rat," Biochemical and Biophysical Research Communications, 1996, 219(1):59-63.

Supplementary European Search Report dated Nov. 30, 2020 in EP 18774871.0.

* cited by examiner

SEQUENCE LISTING

```
<160> NUMBER OF SEQ ID NOS: 49

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45
```

-continued

```
Pro Gln Gly Tyr
        50

<210> SEQ ID NO 2
<211> LENGTH: 1449
<212> TYPE: DNA
<213> ORGANISM: Homo sapiens
<220> FEATURE:
<221> NAME/KEY: CDS
<222> LOCATION: (157)..(711)

<400> SEQUENCE: 2
ctggatagaa cagctcaagc cttgccactt cgggcttctc actgcagctg ggcttggact    60
tcggagtttt gccattgcca gtgggacgtc tgagactttc tccttcaagt acttggcaga   120
tcactctctt agcagggtct gcgcttcgca gccggg atg aag ctg gtt tcc gtc    174
                                       Met Lys Leu Val Ser Val
                                         1               5 gcc ctg atg tac ctg ggt tcg ctc gcc ttc cta ggc gct gac acc gct    222
Ala Leu Met Tyr Leu Gly Ser Leu Ala Phe Leu Gly Ala Asp Thr Ala
          10                  15                  20 cgg ttg gat gtc gcg tcg gag ttt cga aag aag tgg aat aag tgg gct    270
Arg Leu Asp Val Ala Ser Glu Phe Arg Lys Lys Trp Asn Lys Trp Ala
      25                  30                  35 ctg agt cgt ggg aag agg gaa ctg cgg atg tcc agc agc tac ccc acc    318
Leu Ser Arg Gly Lys Arg Glu Leu Arg Met Ser Ser Ser Tyr Pro Thr
  40                  45                  50 ggg ctc gct gac gtg aag gcc ggg cct gcc cag acc ctt att cgg ccc    366
Gly Leu Ala Asp Val Lys Ala Gly Pro Ala Gln Thr Leu Ile Arg Pro
55                  60                  65                  70 cag gac atg aag ggt gcc tct cga agc ccc gaa gac agc agt ccg gat    414
Gln Asp Met Lys Gly Ala Ser Arg Ser Pro Glu Asp Ser Ser Pro Asp
                  75                  80                  85 gcc gcc cgc atc cga gtc aag cgc tac cgc cag agc atg aac aac ttc    462
Ala Ala Arg Ile Arg Val Lys Arg Tyr Arg Gln Ser Met Asn Asn Phe
              90                  95                 100 cag ggc ctc cgg agc ttt ggc tgc cgc ttc ggg acg tgc acg gtg cag    510
Gln Gly Leu Arg Ser Phe Gly Cys Arg Phe Gly Thr Cys Thr Val Gln
         105                 110                 115 aag ctg gca cac cag atc tac cag ttc aca gat aag gac aag gac aac    558
Lys Leu Ala His Gln Ile Tyr Gln Phe Thr Asp Lys Asp Lys Asp Asn
     120                 125                 130 gtc gcc ccc agg agc aag atc agc ccc cag ggc tac ggc cgc cgg cgc    606
Val Ala Pro Arg Ser Lys Ile Ser Pro Gln Gly Tyr Gly Arg Arg Arg
135                 140                 145                 150 cgg cgc tcc ctg ccc gag gcc ggc ccg ggt cgg act ctg gtg tct tct    654
Arg Arg Ser Leu Pro Glu Ala Gly Pro Gly Arg Thr Leu Val Ser Ser
                155                 160                 165 aag cca caa gca cac ggg gct cca gcc ccc ccg agt gga agt gct ccc    702
Lys Pro Gln Ala His Gly Ala Pro Ala Pro Pro Ser Gly Ser Ala Pro
            170                 175                 180 cac ttt ctt taggatttag gcgcccatgg tacaaggaat agtcgcgcaa             751
His Phe Leu
        185 gcatcccgct ggtgcctccc gggacgaagg acttcccgag cggtgtgggg accgggctct   811 gacagccctg cggagaccct gagtccggga ggcaccgtcc ggcggcgagc tctggctttg   871 caagggcccc tccttctggg gcttcgctt ccttagcctt gctcaggtgc aagtgcccca    931 gggggcgggg tgcagaagaa tccgagtgtt tgccaggctt aaggagagga gaaactgaga   991
```

-continued

```
aatgaatgct gagaccccg gagcagggt ctgagccaca gccgtgctcg cccacaaact    1051
gatttctcac ggcgtgtcac cccaccaggg cgcaagcctc actattactt gaactttcca    1111
aaacctaaag aggaaaagtg caatgcgtgt tgtacataca gaggtaacta tcaatattta    1171
agtttgttgc tgtcaagatt ttttttgtaa cttcaaatat agagatattt ttgtacgtta    1231
tatattgtat taagggcatt ttaaaagcaa ttatattgtc ctcccctatt ttaagacgtg    1291
aatgtctcag cgaggtgtaa agttgttcgc cgcgtggaat gtgagtgtgt ttgtgtgcat    1351
gaaagagaaa gactgattac ctcctgtgtg gaagaaggaa acaccgagtc tctgtataat    1411
ctatttacat aaaatgggtg atatgcgaac agcaaacc                            1449
```

<210> SEQ ID NO 3
<211> LENGTH: 185
<212> TYPE: PRT
<213> ORGANISM: Homo sapiens

<400> SEQUENCE: 3

```
Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
                20                  25                  30

Lys Trp Asn Lys Trp Ala Leu Ser Arg Gly Lys Arg Glu Leu Arg Met
            35                  40                  45

Ser Ser Ser Tyr Pro Thr Gly Leu Ala Asp Val Lys Ala Gly Pro Ala
        50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Lys Pro Gln Ala His Gly Ala Pro Ala Pro
                165                 170                 175

Pro Ser Gly Ser Ala Pro His Phe Leu
            180                 185
```

<210> SEQ ID NO 4
<211> LENGTH: 52
<212> TYPE: PRT
<213> ORGANISM: Sus scrofa

<400> SEQUENCE: 4

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                20                  25                  30

Phe Thr Asp Lys Asp Lys Asp Gly Val Ala Pro Arg Ser Lys Ile Ser
            35                  40                  45

Pro Gln Gly Tyr
    50
```

<210> SEQ ID NO 5
<211> LENGTH: 1493
<212> TYPE: DNA
<213> ORGANISM: Sus scrofa

<400> SEQUENCE: 5

| | | | | | |
|---|---|---|---|---|---|
| gcggaacagc | tcgagccttg | ccacctctag | tttcttacca | cagcttggac | gtcggggttt | 60 |
| tgccactgcc | agagggacgt | ctcagacttc | atcttcccaa | atcttggcag | atcacccccct | 120 |
| tagcagggtc | tgcacatctc | agccgggatg | aagctggttc | ccgtagccct | catgtacctg | 180 |
| ggctcgctcg | ccttcctggg | cgctgacaca | gctcggctcg | acgtggcggc | agagttccga | 240 |
| aagaaatgga | ataagtgggc | tctaagtcgt | ggaaaaagag | aacttcggct | gtccagcagc | 300 |
| taccccaccg | ggatcgccga | cttgaaggcc | gggcctgccc | agactgtcat | tcggccccag | 360 |
| gatgtgaagg | ctcctctcg | cagccccag | gccagcattc | cggatgcagc | ccgcatccga | 420 |
| gtcaagcgct | accgccagag | tatgaacaac | ttccagggcc | tgcggagctt | cggctgtcgc | 480 |
| tttgggacgt | gcaccgtgca | gaagctggcg | caccagatct | accagttcac | ggacaaagac | 540 |
| aaggacggcg | tcgccccccg | gagcaagatc | agccccagg | gctacggccg | ccggcgccga | 600 |
| cgctctctgc | ccgaagccag | cctgggccgg | actctgaggt | cccaggagcc | acaggcgcac | 660 |
| ggggcccccgg | cctccccggc | gcatcaagtg | ctcgccactc | tctttaggat | ttaggcgcct | 720 |
| actgtggcag | cagcgaacag | tcgcgcatgc | atcatgccgg | cgcttcctgg | ggcggggggc | 780 |
| ttcccggagc | cgagccctc | agcggctggg | gcccgggcag | agacagcatt | gagagaccga | 840 |
| gagtccggga | ggcacagacc | agcggcgagc | cctgcatttt | caggaacccg | tcctgcttgg | 900 |
| aggcagtgtt | ctcttcggct | taatccagcc | cgggtccccg | ggtggggggtg | gagggtgcag | 960 |
| aggaatccaa | aggagtgtca | tctgccaggc | tcacggagag | gagaaactgc | gaagtaaatg | 1020 |
| cttagacccc | caggggcaag | ggtctgagcc | actgccgtgc | cgcccacaaa | ctgatttctg | 1080 |
| aaggggaata | accccaacag | ggcgcaagcc | tcactattac | ttgaactttc | caaaacctag | 1140 |
| agaggaaaag | tgcaatgtat | gttgtatata | aagaggtaac | tatcaatatt | taagtttgtt | 1200 |
| gctgtcaaga | tttttttttg | taacttcaaa | tatagagata | ttttttgtacg | ttatatattg | 1260 |
| tattaagggc | attttaaaac | aattgtattg | ttcccctccc | ctctatttta | atatgtgaat | 1320 |
| gtctcagcga | ggtgtaacat | tgtttgctgc | gcgaaatgtg | agagtgtgtg | tgtgtgtgtg | 1380 |
| cgtgaaagag | agtctggatg | cctcttgggg | aagaagaaaa | caccatatct | gtataatcta | 1440 |
| tttacataaa | atgggtgata | tgcgaagtag | caaaccaata | aactgtctca | atg | 1493 |

<210> SEQ ID NO 6
<211> LENGTH: 52
<212> TYPE: PRT
<213> ORGANISM: Canis familiaris

<400> SEQUENCE: 6

Tyr Arg Gln Ser Met Asn Asn Phe Gln Gly Pro Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Gly Val Ala Pro Arg Ser Lys Ile Ser
        35                  40                  45

Pro Gln Gly Tyr
    50

<210> SEQ ID NO 7
<211> LENGTH: 1432
<212> TYPE: DNA
<213> ORGANISM: Canis familiaris

<400> SEQUENCE: 7

| | | | | | |
|---|---|---|---|---|---|
| ggttttgcca | gcaccagagc | gacgtctcag | accttctcct | cccggatctt | ggcagatcac | 60 |
| cccctcagca | gggtctgcgc | atcgccgcca | gcatgaagct | ggttcccgtc | gccctcttat | 120 |
| acctgggctc | cctcgccttc | ttgggcgcgg | acaccgcacg | gctagacgtg | gcgtcagagt | 180 |
| tccgaaagaa | gtggaataaa | tgggctgtaa | gtcgtggaaa | gagggaactt | cgagtgtcca | 240 |
| gcagctatcc | caccgggctc | gctgaagtga | aggccgggcc | ggcccagact | cttattcgga | 300 |
| cccaggacgt | gaagggcgcc | tctcgcaacc | cccagaccag | cggtccggac | gccgcccgca | 360 |
| tccgagtcaa | cgctaccgc | cagagtatga | acaatttcca | gggcccgcgg | agcttcggct | 420 |
| gccgcttcgg | aacgtgcacg | gtgcagaaac | tggcgcacca | gatctaccag | ttcacagaca | 480 |
| aggacaagga | cggcgtcgcc | cccaggagca | agattagccc | tcagggctac | ggccgccggc | 540 |
| gccggcgctc | cctgcccgag | cccggccttc | gccggactct | gttgttcccg | gagccacggc | 600 |
| caggcggggc | tccggccccc | cgggcgcatc | aggtgctcgc | caacctcctt | aagatgtagg | 660 |
| cgcctgtggc | agcagcgaac | tggcgcgcgt | gtgcatcccg | ctggcttccc | cctgggcgga | 720 |
| gggcttcccc | gagccgagcc | cctctgccga | tggaagtcgg | gcagagaccg | ggattccggg | 780 |
| aggcaccgtc | ccgcggccag | ccctggcttt | gcgcgagccc | cttctcctcg | gaggcacgga | 840 |
| tccctctgtc | ccaagccggc | ccaggtgtcc | cgtgggggc | agaggaatgc | aagggaggcc | 900 |
| tgccaggctc | acggagagga | ttaactgaga | attaaatgag | aattaaatgc | ttgagaccct | 960 |
| ccccctccc | cccccaggga | cagggtctg | agtcactgcc | gtgcctgccc | acaaactgat | 1020 |
| ttctcacggg | gtgtcacccc | accggggcgc | aagcctcact | attacttgaa | ctttccaaaa | 1080 |
| cctagagagg | aaaagtgcaa | tgcgtgttgt | atatacagag | gtaactatca | atatttaagt | 1140 |
| tcgttgctgt | cagaagattt | tttttgtaac | ttcaaatata | gagatatttt | tgtacgttat | 1200 |
| atattgtatt | aagggcattt | aaaaaccatt | gcattgtccc | cctccccact | tattttaata | 1260 |
| cgtgaatgtc | tcagcgaggt | gtaacgttgt | ttttgctgca | gagtgtgtga | gtgtgcgtga | 1320 |
| gagacttatt | acctcttgtg | gaagaaggaa | caccgtgtct | ctgcattatc | tatttacata | 1380 |
| aaatgggtga | tatgcgaaaa | tagcaaatca | ataataaacg | gtctcgatgc | tg | 1432 |

<210> SEQ ID NO 8
<211> LENGTH: 52
<212> TYPE: PRT
<213> ORGANISM: Bos taurus

<400> SEQUENCE: 8

Tyr Arg Gln Ser Leu Asn Asn Phe Gln Gly Leu Arg Ser Phe Gly Cys
1               5                   10                  15

Arg Phe Gly Thr Cys Thr Val Gln Lys Leu Ala His Gln Ile Tyr His
            20                  25                  30

Phe Thr Asp Lys Asp Lys Asp Gly Ser Ala Pro Arg Ser Lys Ile Ser
        35                  40                  45

Pro Gln Gly Tyr
    50

<210> SEQ ID NO 9
<211> LENGTH: 1439

<212> TYPE: DNA
<213> ORGANISM: Bos taurus

<400> SEQUENCE: 9

```
cgggaaacag ctcgaacctt ctcacttttg gcttctcact gcagcttcga cgtcggggtt    60
ttgccactgc cagaacgccg tctcagactt aatactccaa agaattttgg cagatcaccc   120
cctcagcagg gtctgcgcat cgccgccggg atgaagctgg ttcccgtcgc cctcctgtac   180
ctggggtcgc tcgccttcct aggcgtggac acggcacggc tcgacgtggc ggcagagttc   240
cgaaagaaat ggaataagtg ggctctaagt cgtggaaaaa gagaacttcg cgagtccagt   300
agctaccccca ccgggctcgc cgacgtgaag gccgggcctg tccagactct tattcggccc   360
caggatgtaa agggcgcctc tcgaagccct caggccagca gtcctgacgc agcccgcatc   420
cgagtcaagc gctaccgcca gagtttgaac aacttccagg gcctgcggag cttcggttgt   480
cgcttcggga catgcacggt gcagaagttg gcgcatcaga tctaccattt cacggacaag   540
gacaaggacg gatccgcccc caggagcaag atcagccccc agggctacgg ccgtcggcgc   600
cgacgttcac tgcctgaggc cggcttgggt cggactctat tacagcctcc agagccaaag   660
ctgcgagggg ccccggactc ccgggtgcat caagtacttg ccaccctcag gatttaggcg   720
cctgggcagc agcgaacagt cgcgcacgca tctcgccggc acctcttcgg gcgggagggc   780
ttccgcgagc cgagccctc actcagccta tgggcccggg ctgagaacag ccctgagaga   840
ccgagagtcc aggaggcacc gtccggcagc agcgagcac tggctttgca ggaacccgtc    900
ctcctcggag gggaggcagt gttctcttca ctctaattgg ggccaggtgc agtttctcct    960
ctccgtgagc ctggcagacg ctcacggaga ggagaaactg cgaaataaat gatgagaccc   1020
tcagggggcaa gggtctgagc cactgccgtg cccgcccaca aactgattcc tgatgggggt   1080
gtcaccccac cggggtgcaa gcctcactat tacttgaact ttccgaaacc tagagaggaa   1140
aagtgcaatg agtgttgtat atacagagat aattatcaat atttaaattt gttgttgtca   1200
agatttttt tgtaacttca aatatagaga tatttttgta cgttatatat tgtattaagg   1260
gcattttaaa gcaattgtat tgttcccctc ccctctattt taataagtga atgtctcagc   1320
gagatgcaac gttgtttgct gcgtggaatg tgagagtgtg tgcgtgaaag agatgagttg   1380
cctcttgtgg aagaagaaaa caccgtgtct gtataatcta tttacataaa gtgggccgg   1439
```

<210> SEQ ID NO 10
<211> LENGTH: 50
<212> TYPE: PRT
<213> ORGANISM: Rattus norvegicus

<400> SEQUENCE: 10

```
Tyr Arg Gln Ser Met Asn Gln Gly Ser Arg Ser Thr Gly Cys Arg Phe
1               5                   10                  15
Gly Thr Cys Thr Met Gln Lys Leu Ala His Gln Ile Tyr Gln Phe Thr
            20                  25                  30
Asp Lys Asp Lys Asp Gly Met Ala Pro Arg Asn Lys Ile Ser Pro Gln
        35                  40                  45
Gly Tyr
    50
```

<210> SEQ ID NO 11
<211> LENGTH: 1376
<212> TYPE: DNA
<213> ORGANISM: Rattus norvegicus

<400> SEQUENCE: 11

```
tccagccttt accgctcctg gtttctcggc ttctcatcgc agtcagtctt ggactttgcg      60
ggttttgccg ctgtcagaag gacgtctcgg actttctgct tcaagtgctt gacaactcac     120
cctttcagca gggtatcgga gcatcgctac agaatgaagc tggtttccat cgccctgatg     180
ttattgggtt cgctcgccgt tctcggcgcg gacaccgcac ggctcgacac ttcctcgcag     240
ttccgaaaga agtggaataa gtgggcgcta agtcgtggga agaggaact acaagcgtcc      300
agcagctacc ctacggggct cgttgatgag aagacagtcc cgacccagac tcttgggctc     360
caggacaagc agagcacgtc tagcacccca caagccagca ctcagagcac agcccacatt     420
cgagtcaaac gctaccgcca gagcatgaac caggggtccc gcagcactgg atgccgcttt     480
gggacctgca caatgcagaa actggctcac cagatctacc agtttacaga caaagacaag     540
gacggcatgg cccccagaaa caagatcagc cctcaaggct atggccgccg cgccggcgt      600
tccctgccag aggtcctccg agcccggact gtggagtcct cccaggagca gacacactca     660
gctccagcct cccggcgca ccaagacatc tccagagtct ctaggttata ggtgcgggtg      720
gcagcattga acagtcgggc gagtatccca ttggcgcctg cggaatcaga gagcttcgca     780
ccctgagcgg actgagacaa tcttgcagag atctgcctgg ctgcccctag ggaggcaga     840
ggaacccaag atcaagccag gctcacgtca gaaaccgaga attacaggct gatactctct     900
ccgggcaggt gtctgagcca ctgccttgcc cgctcataaa ctggttttct cacggggcat     960
acggctcatt acttacttga actttccaaa acctagcgag gaaaagtgca atgcttgtta    1020
tacagccaaa ggtaactatc atatttaagt ttgttgatgt caagaggttt ttttttttgt    1080
aacttcaaat atatagaaat attttttgtac gttatatatt gtattaaggg cattttaaag   1140
cgattatatt gtcaccttcc cctatttttaa gaagtgaatg tctcagcaag gtgtaaggtt   1200
gtttggttcc gtgtgtgtgt gtgtgtgtgt gtgtgtgtgt gtgtgtgtgt gtgtgtaagg    1260
tggagagcgc ctgattaccg cctgtggatg aagaaaaaac attgtgtctt ctataatcta    1320
tttacataaa atatgtgatc tgggaaaaag caaaccaata aactgtctca atgctg         1376
```

<210> SEQ ID NO 12
<211> LENGTH: 50
<212> TYPE: PRT
<213> ORGANISM: Mus musculus

<400> SEQUENCE: 12

```
Tyr Arg Gln Ser Met Asn Gln Gly Ser Arg Ser Asn Gly Cys Arg Phe
1               5                   10                  15
Gly Thr Cys Thr Phe Gln Lys Leu Ala His Gln Ile Tyr Gln Leu Thr
            20                  25                  30
Asp Lys Asp Lys Asp Gly Met Ala Pro Arg Asn Lys Ile Ser Pro Gln
        35                  40                  45
Gly Tyr
    50
```

<210> SEQ ID NO 13
<211> LENGTH: 1381
<212> TYPE: DNA
<213> ORGANISM: Mus musculus

<400> SEQUENCE: 13

```
cttggtgaca ctagacagag caactccagc gttaccgctc ccgctcctgg tttctcggct      60
tctcatcgca gtcaatcttg gactttgggg ttttgctact gtcagaagga cttctttctg     120
```

```
cttcaagtgc ttgacaacgc accccnttat cagggtatca gagcatcgcc acagaatgaa    180
gctggtttcc atcaccctga tgttattggg ttcactcgct ttcctaggcg cggacactgc    240
agggccagat actccttcgc agttccgaaa gaagtggaat aagtgggcgc taagtcgtgg    300
gaagagggaa ctacaagcat ccagcagcta ccctacggga ctcgctgatg agacgacagt    360
tcctacccag actcttgatc cattcctgga cgagcagaac acaactggcc cctacaagc     420
cagcaatcag agcgaagccc acattcgtgt caaacgctac cgccagagca tgaaccaggg    480
ttcccgcagc aatggatgcc gcttcgggac ctgcacattt cagaaattgg cccaccagat    540
ctaccagcta acagacaaag acaaggacgg catggctccc agaaacaaga tcagccctca    600
aggctatggc cgccggcgcc ggcgttccct gctggaggtc ctccggtccc ggactgtgga    660
gtcctcccag gagcagacac acacagcccc aggcccctgg gcgcacatct ccagactctt    720
taggatatag gtgcgggtga cagcattgaa cagtcgggcg agtatcccgt ggcgcctgc     780
ggaatcagaa aacttcgcac cggggcggac tgagacaatc ctgcagagat ctgcctggct    840
gcccctaggg gaggcagagg aacccaagac caagccaggc tcatgccaga aaccgagact    900
tacaggctga tactctccgg gcaggggtct gagccactgc cttgcccgct cataaactgg    960
tttctcacgg ggcataagcc tcattactac ttgaactttc caaaacctag cgaggaacgt   1020
gcaatgcttg ttgtccagcc aaaggtaact atagtattta agtttgttgc tgtcaaggtt   1080
tttttttttg taacttcaaa tatatagaga tattttgta cgttatatat tgtattaagg    1140
gcattttaaa gtgattatat tgtcaccttc ccctatttta agacgtgaat gtctcagcaa   1200
ggtgtaaggt tgtttggttc cgtgtgtgtg tgtgtgtgtg tgtgtgtgtg tgtgtgtgtg   1260
taaggtggag agcgcctgat tatcgcctgt ggatgaagaa aaacattgt gtttcctata    1320
atctatttac ataaaatatg tgatctggga aaaagcaaac caataaactg tctcaatgct   1380
g                                                                   1381

<210> SEQ ID NO 14
<211> LENGTH: 891
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(891)

<400> SEQUENCE: 14 atg gac aaa act cac aca tgc cca ccg tgc cca gca cct gaa ctc ctg     48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc     96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc    144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag    192
His Glu Asp Pro Glu Val Lys Phe Asn Trp Tyr Val Asp Gly Val Glu
    50                  55                  60 gtg cat aat gcc aag aca aag ccg cgg gag gag cag tac aac agc acg    240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat    288
```

```
                Tyr Arg Val Val Ser Val Leu Thr Val Leu His Gln Asp Trp Leu Asn
                                85                  90                  95 gcc aag gag tac aag tgc aag gtc tcc aac aaa gcc ctc cca gcc ccc            336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag            384
Ile Glu Lys Thr Ile Ser Lys Ala Lys Gly Gln Pro Arg Glu Pro Gln
            115                 120                 125 gtg tac acc ctg ccc cca tcc cgg gag gag atg acc aag aac cag gtc            432
Val Tyr Thr Leu Pro Pro Ser Arg Glu Glu Met Thr Lys Asn Gln Val
        130                 135                 140 agc ctg acc tgc ctg gtc aaa ggc ttc tat ccc agc gac atc gcc gtg            480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct            528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc            576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg            624
Val Asp Lys Ser Arg Trp Gln Gln Gly Asn Val Phe Ser Cys Ser Val
            195                 200                 205 atg cat gag gct ctg cac aac cac tac acg cag aag agc ctc tcc ctg            672
Met His Glu Ala Leu His Asn His Tyr Thr Gln Lys Ser Leu Ser Leu
        210                 215                 220 tct ccg ggt aaa gga gga gga tca gga gga gga tca gga gga                    720
Ser Pro Gly Lys Gly Gly Gly Ser Gly Gly Gly Ser Gly Gly
225                 230                 235                 240 gga gga tca tac cgc cag agc atg aac aac ttc cag ggc ctc cga tcg            768
Gly Gly Ser Tyr Arg Gln Ser Met Asn Asn Phe Gln Gly Leu Arg Ser
                245                 250                 255 ttt ggc tgc cgc ttc ggg acg tgc acg gtg cag aag ctg gca cac cag            816
Phe Gly Cys Arg Phe Gly Thr Cys Thr Val Gln Lys Leu Ala His Gln
            260                 265                 270 atc tac cag ttc aca gat aag gac aag gac aac gtc gcc ccc agg agc            864
Ile Tyr Gln Phe Thr Asp Lys Asp Lys Asp Asn Val Ala Pro Arg Ser
        275                 280                 285 aag atc agc ccc cag ggc tac ggc tga                                        891
Lys Ile Ser Pro Gln Gly Tyr Gly
    290                 295

<210> SEQ ID NO 15
<211> LENGTH: 296
<212> TYPE: PRT
<213> ORGANISM: Artificial
<220> FEATURE:
<223> OTHER INFORMATION: Synthetic Construct

<400> SEQUENCE: 15

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Ser Gly Gly Gly Gly Ser Gly Gly Gly
225                 230                 235                 240

Gly Gly Ser Tyr Arg Gln Ser Met Asn Asn Phe Gln Gly Leu Arg Ser
                245                 250                 255

Phe Gly Cys Arg Phe Gly Thr Cys Thr Val Gln Lys Leu Ala His Gln
            260                 265                 270

Ile Tyr Gln Phe Thr Asp Lys Asp Lys Asp Asn Val Ala Pro Arg Ser
        275                 280                 285

Lys Ile Ser Pro Gln Gly Tyr Gly
    290                 295

<210> SEQ ID NO 16
<211> LENGTH: 891
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(891)

<400> SEQUENCE: 16 atg gac aaa act cac aca tgc cca ccg tgc cca gca cct gaa ctc ctg      48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
            20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
    50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                85                  90                  95
```

| | |
|---|---|
| ggc aag gag tac aag tgc aag gtc tcc aac aaa gcc ctc cca gcc ccc<br>Gly Lys Glu Tyr Lys Cys Lys Val Ser Asn Lys Ala Leu Pro Ala Pro<br>                   100                     105               110 | 336 |
| atc gag aaa acc atc tcc aaa gcc aaa ggg cag ccc cga gaa cca cag<br>Ile Glu Lys Thr Ile Ser Lys Ala Lys Gly Gln Pro Arg Glu Pro Gln<br>         115                    120                125 | 384 |
| gtg tac acc ctg ccc cca tcc cgg gag gag atg acc aag aac cag gtc<br>Val Tyr Thr Leu Pro Pro Ser Arg Glu Glu Met Thr Lys Asn Gln Val<br>130                     135                    140 | 432 |
| agc ctg acc tgc ctg gtc aaa ggc ttc tat ccc agc gac atc gcc gtg<br>Ser Leu Thr Cys Leu Val Lys Gly Phe Tyr Pro Ser Asp Ile Ala Val<br>145                    150                155               160 | 480 |
| gag tgg gag agc aat ggg cag ccg gag aac aac tac aag acc acg cct<br>Glu Trp Glu Ser Asn Gly Gln Pro Glu Asn Asn Tyr Lys Thr Thr Pro<br>                   165                    170               175 | 528 |
| ccc gtg ctg gac tcc gac ggc tcc ttc ttc ctc tac agc aag ctc acc<br>Pro Val Leu Asp Ser Asp Gly Ser Phe Phe Leu Tyr Ser Lys Leu Thr<br>                   180                    185               190 | 576 |
| gtg gac aag agc agg tgg cag cag ggg aac gtc ttc tca tgc tcc gtg<br>Val Asp Lys Ser Arg Trp Gln Gln Gly Asn Val Phe Ser Cys Ser Val<br>195                    200                205 | 624 |
| atg cat gag gct ctg cac aac cac tac acg cag aag agc ctc tcc ctg<br>Met His Glu Ala Leu His Asn His Tyr Thr Gln Lys Ser Leu Ser Leu<br>210                    215                   220 | 672 |
| tct ccg ggt aaa gga gga gga tca gga gga gga tca gga gga<br>Ser Pro Gly Lys Gly Gly Gly Ser Gly Gly Gly Ser Gly Gly<br>225                    230                235               240 | 720 |
| gga gga aag tac cgc cag agc atg aac aac ttc cag ggc ctc cga tcg<br>Gly Gly Lys Tyr Arg Gln Ser Met Asn Asn Phe Gln Gly Leu Arg Ser<br>                   245                    250               255 | 768 |
| ttt ggc tgc cgc ttc ggg acg tgc acg gtg cag aag ctg gca cac cag<br>Phe Gly Cys Arg Phe Gly Thr Cys Thr Val Gln Lys Leu Ala His Gln<br>                   260                    265               270 | 816 |
| atc tac cag ttc aca gat aag gac aag gac aac gtc gcc ccc agg agc<br>Ile Tyr Gln Phe Thr Asp Lys Asp Lys Asp Asn Val Ala Pro Arg Ser<br>         275                    280                285 | 864 |
| aag atc agc ccc cag ggc tac ggc tga<br>Lys Ile Ser Pro Gln Gly Tyr Gly<br>         290                    295 | 891 |

<210> SEQ ID NO 17
<211> LENGTH: 296
<212> TYPE: PRT
<213> ORGANISM: Artificial
<220> FEATURE:
<223> OTHER INFORMATION: Synthetic Construct

<400> SEQUENCE: 17

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn

```
                        85                  90                  95
Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Ser Gly Gly Gly Ser Gly Gly
225                 230                 235                 240

Gly Gly Lys Tyr Arg Gln Ser Met Asn Asn Phe Gln Gly Leu Arg Ser
                245                 250                 255

Phe Gly Cys Arg Phe Gly Thr Cys Thr Val Lys Leu Ala His Gln
            260                 265                 270

Ile Tyr Gln Phe Thr Asp Lys Asp Lys Asp Asn Val Ala Pro Arg Ser
        275                 280                 285

Lys Ile Ser Pro Gln Gly Tyr Gly
    290                 295

<210> SEQ ID NO 18
<211> LENGTH: 882
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(882)

<400> SEQUENCE: 18 atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc     96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac    144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat    192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg    240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag    288
Val Ser Val Leu Thr Val Leu His Gln Asp Trp Leu Asn Gly Lys Glu
                85                  90                  95 tac aag tgc aag gtc tcc aac aaa ggc ctc ccg tcc tcc atc gag aaa    336
Tyr Lys Cys Lys Val Ser Asn Lys Gly Leu Pro Ser Ser Ile Glu Lys
```

```
                Tyr Lys Cys Lys Val Ser Asn Lys Gly Leu Pro Ser Ser Ile Glu Lys
                                100                 105                 110 acc atc tcc aaa gcc aaa ggg cag ccc cga gag cca cag gtg tac acc          384
Thr Ile Ser Lys Ala Lys Gly Gln Pro Arg Glu Pro Gln Val Tyr Thr
            115                 120                 125 ctg ccc cca tcc cag gag gag atg acc aag aac cag gtc agc ctg acc          432
Leu Pro Pro Ser Gln Glu Glu Met Thr Lys Asn Gln Val Ser Leu Thr
130                 135                 140 tgc ctg gtc aaa ggc ttc tac ccc agc gac atc gcc gtg gag tgg gag          480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg          528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag          576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag          624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt          672
Ala Leu His Asn His Tyr Thr Gln Lys Ser Leu Ser Leu Ser Pro Gly
210                 215                 220 aaa gga gga gga gga tca gga gga gga gga tca gga gga gga gga tca          720
Lys Gly Gly Gly Gly Ser Gly Gly Gly Gly Ser Gly Gly Gly Gly Ser
225                 230                 235                 240 tac cgc cag agc atg aac aac ttc cag ggc ctc cgg agc ttt ggc tgc          768
Tyr Arg Gln Ser Met Asn Asn Phe Gln Gly Leu Arg Ser Phe Gly Cys
                245                 250                 255 cgc ttc ggg acg tgc acg gtg cag aag ctg gca cac cag atc tac cag          816
Arg Phe Gly Thr Cys Thr Val Gln Lys Leu Ala His Gln Ile Tyr Gln
            260                 265                 270 ttc aca gat aag gac aag gac aac gtc gcc ccc agg agc aag atc agc          864
Phe Thr Asp Lys Asp Lys Asp Asn Val Ala Pro Arg Ser Lys Ile Ser
        275                 280                 285 ccc cag ggc tac ggc tga                                                  882
Pro Gln Gly Tyr Gly
    290

<210> SEQ ID NO 19
<211> LENGTH: 293
<212> TYPE: PRT
<213> ORGANISM: Artificial
<220> FEATURE:
<223> OTHER INFORMATION: Synthetic Construct

<400> SEQUENCE: 19

Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95
```

```
Tyr Lys Cys Lys Val Ser Asn Lys Gly Leu Pro Ser Ser Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Gly Ser Gly Gly Gly Ser Gly Gly Gly Ser
225                 230                 235                 240

Tyr Arg Gln Ser Met Asn Asn Phe Gln Gly Leu Arg Ser Phe Gly Cys
                245                 250                 255

Arg Phe Gly Thr Cys Thr Val Gln Lys Leu Ala His Gln Ile Tyr Gln
            260                 265                 270

Phe Thr Asp Lys Asp Lys Asp Asn Val Ala Pro Arg Ser Lys Ile Ser
        275                 280                 285

Pro Gln Gly Tyr Gly
    290

<210> SEQ ID NO 20
<211> LENGTH: 882
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(882)

<400> SEQUENCE: 20 atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc      96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac     144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat     192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg     240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag     288
Val Ser Val Leu Thr Val Leu His Gln Asp Trp Leu Asn Gly Lys Glu
            85                  90                  95 tac aag tgc aag gtc tcc aac aaa ggc ctc ccg tcc tcc atc gag aaa     336
Tyr Lys Cys Lys Val Ser Asn Lys Gly Leu Pro Ser Ser Ile Glu Lys
        100                 105                 110
```

```
acc atc tcc aaa gcc aaa ggg cag ccc cga gag cca cag gtg tac acc      384
Thr Ile Ser Lys Ala Lys Gly Gln Pro Arg Glu Pro Gln Val Tyr Thr
        115                 120                 125 ctg ccc cca tcc cag gag gag atg acc aag aac cag gtc agc ctg acc      432
Leu Pro Pro Ser Gln Glu Glu Met Thr Lys Asn Gln Val Ser Leu Thr
130                 135                 140 tgc ctg gtc aaa ggc ttc tac ccc agc gac atc gcc gtg gag tgg gag      480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg      528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag      576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag      624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt      672
Ala Leu His Asn His Tyr Thr Gln Lys Ser Leu Ser Leu Ser Pro Gly
    210                 215                 220 aaa gga gga gga gga tca gga gga gga gga tca gga gga gga aag         720
Lys Gly Gly Gly Gly Ser Gly Gly Gly Gly Ser Gly Gly Gly Gly Lys
225                 230                 235                 240 tac cgc cag agc atg aac aac ttc cag ggc ctc cgg agc ttt ggc tgc      768
Tyr Arg Gln Ser Met Asn Asn Phe Gln Gly Leu Arg Ser Phe Gly Cys
                245                 250                 255 cgc ttc ggg acg tgc acg gtg cag aag ctg gca cac cag atc tac cag      816
Arg Phe Gly Thr Cys Thr Val Gln Lys Leu Ala His Gln Ile Tyr Gln
            260                 265                 270 ttc aca gat aag gac aag gac aac gtc gcc ccc agg agc aag atc agc      864
Phe Thr Asp Lys Asp Lys Asp Asn Val Ala Pro Arg Ser Lys Ile Ser
        275                 280                 285 ccc cag ggc tac ggc tga                                              882
Pro Gln Gly Tyr Gly
    290

<210> SEQ ID NO 21
<211> LENGTH: 293
<212> TYPE: PRT
<213> ORGANISM: Artificial
<220> FEATURE:
<223> OTHER INFORMATION: Synthetic Construct

<400> SEQUENCE: 21

Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110
```

```
Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Gly Gly Ser Gly Gly Gly Gly Ser Gly Gly Gly Gly Lys
225                 230                 235                 240

Tyr Arg Gln Ser Met Asn Asn Phe Gln Gly Leu Arg Ser Phe Gly Cys
                245                 250                 255

Arg Phe Gly Thr Cys Thr Val Gln Lys Leu Ala His Gln Ile Tyr Gln
            260                 265                 270

Phe Thr Asp Lys Asp Lys Asp Asn Val Ala Pro Arg Ser Lys Ile Ser
        275                 280                 285

Pro Gln Gly Tyr Gly
    290
```

```
<210> SEQ ID NO 22
<211> LENGTH: 15
<212> TYPE: PRT
<213> ORGANISM: Artificial
<220> FEATURE:
<223> OTHER INFORMATION: linker

<400> SEQUENCE: 22

Gly Gly Gly Gly Ser Gly Gly Gly Gly Ser Gly Gly Gly Gly Ser
1               5                   10                  15

<210> SEQ ID NO 23
<211> LENGTH: 45
<212> TYPE: DNA
<213> ORGANISM: Artificial
<220> FEATURE:
<223> OTHER INFORMATION: linker

<400> SEQUENCE: 23
ggaggaggag gatcaggagg aggaggatca ggaggaggag gatca              45

<210> SEQ ID NO 24
<211> LENGTH: 15
<212> TYPE: PRT
<213> ORGANISM: Artificial
<220> FEATURE:
<223> OTHER INFORMATION: linker

<400> SEQUENCE: 24

Gly Gly Gly Gly Ser Gly Gly Gly Gly Ser Gly Gly Gly Gly Lys
1               5                   10                  15

<210> SEQ ID NO 25
<211> LENGTH: 45
<212> TYPE: DNA
```

```
<213> ORGANISM: Artificial
<220> FEATURE:
<223> OTHER INFORMATION: linker

<400> SEQUENCE: 25
ggaggaggag gatcaggagg aggaggatca ggaggaggag gaaag          45

<210> SEQ ID NO 26
<211> LENGTH: 4
<212> TYPE: PRT
<213> ORGANISM: Artificial
<220> FEATURE:
<223> OTHER INFORMATION: linker

<400> SEQUENCE: 26

Gly Gly Gly Ser
1

<210> SEQ ID NO 27
<211> LENGTH: 5
<212> TYPE: PRT
<213> ORGANISM: Artificial
<220> FEATURE:
<223> OTHER INFORMATION: linker

<400> SEQUENCE: 27

Gly Gly Gly Gly Ser
1               5

<210> SEQ ID NO 28
<211> LENGTH: 4
<212> TYPE: PRT
<213> ORGANISM: Artificial
<220> FEATURE:
<223> OTHER INFORMATION: linker

<400> SEQUENCE: 28

Gly Gly Gly Lys
1

<210> SEQ ID NO 29
<211> LENGTH: 5
<212> TYPE: PRT
<213> ORGANISM: Artificial
<220> FEATURE:
<223> OTHER INFORMATION: linker

<400> SEQUENCE: 29

Gly Gly Gly Gly Lys
1               5

<210> SEQ ID NO 30
<211> LENGTH: 876
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(876)

<400> SEQUENCE: 30 atg gac aaa act cac aca tgc cca ccg tgc cca gca cct gaa ctc ctg      48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
```

```
                 20                  25                  30
atg atc tcc cgg acc cct gag gtc aca tgc gtg gtg gtg gac gtg agc    144
Met Ile Ser Arg Thr Pro Glu Val Thr Cys Val Val Val Asp Val Ser
         35                  40                  45 cac gaa gac cct gag gtc aag ttc aac tgg tac gtg gac ggc gtg gag    192
His Glu Asp Pro Glu Val Lys Phe Asn Trp Tyr Val Asp Gly Val Glu
 50                  55                  60 gtg cat aat gcc aag aca aag ccg cgg gag gag cag tac aac agc acg    240
Val His Asn Ala Lys Thr Lys Pro Arg Glu Glu Gln Tyr Asn Ser Thr
 65                  70                  75                  80 tac cgt gtg gtc agc gtc ctc acc gtc ctg cac cag gac tgg ctg aat    288
Tyr Arg Val Val Ser Val Leu Thr Val Leu His Gln Asp Trp Leu Asn
                     85                  90                  95 ggc aag gag tac aag tgc aag gtc tcc aac aaa gcc ctc cca gcc ccc    336
Gly Lys Glu Tyr Lys Cys Lys Val Ser Asn Lys Ala Leu Pro Ala Pro
                100                 105                 110 atc gag aaa acc atc tcc aaa gcc aaa ggg cag ccc cga gaa cca cag    384
Ile Glu Lys Thr Ile Ser Lys Ala Lys Gly Gln Pro Arg Glu Pro Gln
            115                 120                 125 gtg tac acc ctg ccc cca tcc cgg gag gag atg acc aag aac cag gtc    432
Val Tyr Thr Leu Pro Pro Ser Arg Glu Glu Met Thr Lys Asn Gln Val
        130                 135                 140 agc ctg acc tgc ctg gtc aaa ggc ttc tat ccc agc gac atc gcc gtg    480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct    528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc    576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg    624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg    672
Met His Glu Ala Leu His Asn His Tyr Thr Gln Lys Ser Leu Ser Leu
    210                 215                 220 tct ccg ggt aaa gga gga gga tca gga gga gga tca gga gga              720
Ser Pro Gly Lys Gly Gly Gly Ser Gly Gly Gly Ser Gly Gly
225                 230                 235                 240 gga gga tca aac aac ttc cag ggc ctc cga tcg ttt ggc tgc cgc ttc    768
Gly Gly Ser Asn Asn Phe Gln Gly Leu Arg Ser Phe Gly Cys Arg Phe
                245                 250                 255 ggg acg tgc acg gtg cag aag ctg gca cac cag atc tac cag ttc aca    816
Gly Thr Cys Thr Val Gln Lys Leu Ala His Gln Ile Tyr Gln Phe Thr
            260                 265                 270 gat aag gac aag gac aac gtc gcc ccc agg agc aag atc agc ccc cag    864
Asp Lys Asp Lys Asp Asn Val Ala Pro Arg Ser Lys Ile Ser Pro Gln
        275                 280                 285 ggc tac ggc tga                                                     876
Gly Tyr Gly
    290
```

<210> SEQ ID NO 31
<211> LENGTH: 291
<212> TYPE: PRT
<213> ORGANISM: Artificial
<220> FEATURE:
<223> OTHER INFORMATION: Synthetic Construct

<400> SEQUENCE: 31

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Ser Gly Gly Gly Gly Ser Gly Gly
225                 230                 235                 240

Gly Gly Ser Asn Asn Phe Gln Gly Leu Arg Ser Phe Gly Cys Arg Phe
            245                 250                 255

Gly Thr Cys Thr Val Gln Lys Leu Ala His Gln Ile Tyr Gln Phe Thr
        260                 265                 270

Asp Lys Asp Lys Asp Asn Val Ala Pro Arg Ser Lys Ile Ser Pro Gln
    275                 280                 285

Gly Tyr Gly
    290
```

<210> SEQ ID NO 32
<211> LENGTH: 876
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(876)

<400> SEQUENCE: 32

```
atg gac aaa act cac aca tgc cca ccg tgc cca gca cct gaa ctc ctg    48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc    96
Gly Gly Pro Ser Val Phe Leu Phe Pro Pro Lys Pro Lys Asp Thr Leu
            20                  25                  30
```

```
atg atc tcc cgg acc cct gag gtc aca tgc gtg gtg gtg gac gtg agc    144
Met Ile Ser Arg Thr Pro Glu Val Thr Cys Val Val Val Asp Val Ser
        35                  40                  45 cac gaa gac cct gag gtc aag ttc aac tgg tac gtg gac ggc gtg gag    192
His Glu Asp Pro Glu Val Lys Phe Asn Trp Tyr Val Asp Gly Val Glu
 50                  55                  60 gtg cat aat gcc aag aca aag ccg cgg gag gag cag tac aac agc acg    240
Val His Asn Ala Lys Thr Lys Pro Arg Glu Glu Gln Tyr Asn Ser Thr
 65                  70                  75                  80 tac cgt gtg gtc agc gtc ctc acc gtc ctg cac cag gac tgg ctg aat    288
Tyr Arg Val Val Ser Val Leu Thr Val Leu His Gln Asp Trp Leu Asn
                     85                  90                  95 ggc aag gag tac aag tgc aag gtc tcc aac aaa gcc ctc cca gcc ccc    336
Gly Lys Glu Tyr Lys Cys Lys Val Ser Asn Lys Ala Leu Pro Ala Pro
                100                 105                 110 atc gag aaa acc atc tcc aaa gcc aaa ggg cag ccc cga gaa cca cag    384
Ile Glu Lys Thr Ile Ser Lys Ala Lys Gly Gln Pro Arg Glu Pro Gln
            115                 120                 125 gtg tac acc ctg ccc cca tcc cgg gag gag atg acc aag aac cag gtc    432
Val Tyr Thr Leu Pro Pro Ser Arg Glu Glu Met Thr Lys Asn Gln Val
        130                 135                 140 agc ctg acc tgc ctg gtc aaa ggc ttc tat ccc agc gac atc gcc gtg    480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct    528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc    576
Pro Val Leu Asp Ser Asp Gly Ser Phe Phe Leu Tyr Ser Lys Leu Thr
                180                 185                 190 gtg gac aag agc agg tgg cag cag ggg aac gtc ttc tca tgc tcc gtg    624
Val Asp Lys Ser Arg Trp Gln Gln Gly Asn Val Phe Ser Cys Ser Val
            195                 200                 205 atg cat gag gct ctg cac aac cac tac acg cag aag agc ctc tcc ctg    672
Met His Glu Ala Leu His Asn His Tyr Thr Gln Lys Ser Leu Ser Leu
        210                 215                 220 tct ccg ggt aaa gga gga gga tca gga gga gga gga tca gga gga        720
Ser Pro Gly Lys Gly Gly Gly Gly Ser Gly Gly Gly Gly Ser Gly Gly
225                 230                 235                 240 gga gga aag aac aac ttc cag ggc ctc cga tcg ttt ggc tgc cgc ttc    768
Gly Gly Lys Asn Asn Phe Gln Gly Leu Arg Ser Phe Gly Cys Arg Phe
                245                 250                 255 ggg acg tgc acg gtg cag aag ctg gca cac cag atc tac cag ttc aca    816
Gly Thr Cys Thr Val Gln Lys Leu Ala His Gln Ile Tyr Gln Phe Thr
                260                 265                 270 gat aag gac aag gac aac gtc gcc ccc agg agc aag atc agc ccc cag    864
Asp Lys Asp Lys Asp Asn Val Ala Pro Arg Ser Lys Ile Ser Pro Gln
            275                 280                 285 ggc tac ggc tga                                                    876
Gly Tyr Gly
        290
```

<210> SEQ ID NO 33
<211> LENGTH: 291
<212> TYPE: PRT
<213> ORGANISM: Artificial
<220> FEATURE:
<223> OTHER INFORMATION: Synthetic Construct

<400> SEQUENCE: 33

Met Asp Lys Thr His Thr Cys Pro Pro Cys Pro Ala Pro Glu Leu Leu

```
                1               5                  10                 15
            Gly Gly Pro Ser Val Phe Leu Phe Pro Pro Lys Pro Lys Asp Thr Leu
                            20                 25                 30

Met Ile Ser Arg Thr Pro Glu Val Thr Cys Val Val Val Asp Val Ser
                            35                 40                 45

His Glu Asp Pro Glu Val Lys Phe Asn Trp Tyr Val Asp Gly Val Glu
                50                 55                 60

Val His Asn Ala Lys Thr Lys Pro Arg Glu Glu Gln Tyr Asn Ser Thr
            65                  70                 75                  80

Tyr Arg Val Val Ser Val Leu Thr Val Leu His Gln Asp Trp Leu Asn
                            85                 90                 95

Gly Lys Glu Tyr Lys Cys Lys Val Ser Asn Lys Ala Leu Pro Ala Pro
                            100                105                110

Ile Glu Lys Thr Ile Ser Lys Ala Lys Gly Gln Pro Arg Glu Pro Gln
                            115                120                125

Val Tyr Thr Leu Pro Pro Ser Arg Glu Glu Met Thr Lys Asn Gln Val
                            130                135                140

Ser Leu Thr Cys Leu Val Lys Gly Phe Tyr Pro Ser Asp Ile Ala Val
            145                 150                155                 160

Glu Trp Glu Ser Asn Gly Gln Pro Glu Asn Asn Tyr Lys Thr Thr Pro
                            165                170                175

Pro Val Leu Asp Ser Asp Gly Ser Phe Phe Leu Tyr Ser Lys Leu Thr
                            180                185                190

Val Asp Lys Ser Arg Trp Gln Gln Gly Asn Val Phe Ser Cys Ser Val
                            195                200                205

Met His Glu Ala Leu His Asn His Tyr Thr Gln Lys Ser Leu Ser Leu
                            210                215                220

Ser Pro Gly Lys Gly Gly Gly Ser Gly Gly Gly Ser Gly Gly Gly Ser Gly
            225                 230                235                 240

Gly Gly Lys Asn Asn Phe Gln Gly Leu Arg Ser Phe Gly Cys Arg Phe
                            245                250                255

Gly Thr Cys Thr Val Gln Lys Leu Ala His Gln Ile Tyr Gln Phe Thr
                            260                265                270

Asp Lys Asp Lys Asp Asn Val Ala Pro Arg Ser Lys Ile Ser Pro Gln
                            275                280                285

Gly Tyr Gly
                290

<210> SEQ ID NO 34
<211> LENGTH: 861
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(861)

<400> SEQUENCE: 34 atg gac aaa act cac aca tgc cca ccg tgc cca gca cct gaa ctc ctg    48
Met Asp Lys Thr His Thr Cys Pro Pro Cys Pro Ala Pro Glu Leu Leu
1               5                  10                 15 ggg gga ccg tca gtc ttc ctc ttc ccc cca aaa ccc aag gac acc ctc    96
Gly Gly Pro Ser Val Phe Leu Phe Pro Pro Lys Pro Lys Asp Thr Leu
                20                 25                 30 atg atc tcc cgg acc cct gag gtc aca tgc gtg gtg gtg gac gtg agc    144
Met Ile Ser Arg Thr Pro Glu Val Thr Cys Val Val Val Asp Val Ser
                35                 40                 45
```

```
cac gaa gac cct gag gtc aag ttc aac tgg tac gtg gac ggc gtg gag       192
His Glu Asp Pro Glu Val Lys Phe Asn Trp Tyr Val Asp Gly Val Glu
 50                  55                  60 gtg cat aat gcc aag aca aag ccg cgg gag gag cag tac aac agc acg       240
Val His Asn Ala Lys Thr Lys Pro Arg Glu Glu Gln Tyr Asn Ser Thr
 65                  70                  75                  80 tac cgt gtg gtc agc gtc ctc acc gtc ctg cac cag gac tgg ctg aat       288
Tyr Arg Val Val Ser Val Leu Thr Val Leu His Gln Asp Trp Leu Asn
                 85                  90                  95 ggc aag gag tac aag tgc aag gtc tcc aac aaa gcc ctc cca gcc ccc       336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag       384
Ile Glu Lys Thr Ile Ser Lys Ala Lys Gly Gln Pro Arg Glu Pro Gln
        115                 120                 125 gtg tac acc ctg ccc cca tcc cgg gag gag atg acc aag aac cag gtc       432
Val Tyr Thr Leu Pro Pro Ser Arg Glu Glu Met Thr Lys Asn Gln Val
130                 135                 140 agc ctg acc tgc ctg gtc aaa ggc ttc tat ccc agc gac atc gcc gtg       480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct       528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc       576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg       624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg       672
Met His Glu Ala Leu His Asn His Tyr Thr Gln Lys Ser Leu Ser Leu
210                 215                 220 tct ccg ggt aaa gga gga gga tca gga gga gga gga tca gga gga            720
Ser Pro Gly Lys Gly Gly Gly Ser Gly Gly Gly Gly Ser Gly Gly
225                 230                 235                 240 gga gga tca ctc cga tcg ttt ggc tgc cgc ttc ggg acg tgc acg gtg       768
Gly Gly Ser Leu Arg Ser Phe Gly Cys Arg Phe Gly Thr Cys Thr Val
                245                 250                 255 cag aag ctg gca cac cag atc tac cag ttc aca gat aag gac aag gac       816
Gln Lys Leu Ala His Gln Ile Tyr Gln Phe Thr Asp Lys Asp Lys Asp
            260                 265                 270 aac gtc gcc ccc agg agc aag atc agc ccc cag ggc tac ggc tga           861
Asn Val Ala Pro Arg Ser Lys Ile Ser Pro Gln Gly Tyr Gly
        275                 280                 285
```

<210> SEQ ID NO 35
<211> LENGTH: 286
<212> TYPE: PRT
<213> ORGANISM: Artificial
<220> FEATURE:
<223> OTHER INFORMATION: Synthetic Construct

<400> SEQUENCE: 35

```
Met Asp Lys Thr His Thr Cys Pro Pro Cys Pro Ala Pro Glu Leu Leu
  1               5                  10                  15

Gly Gly Pro Ser Val Phe Leu Phe Pro Pro Lys Pro Lys Asp Thr Leu
                 20                  25                  30

Met Ile Ser Arg Thr Pro Glu Val Thr Cys Val Val Val Asp Val Ser
```

```
               35                  40                  45
His Glu Asp Pro Glu Val Lys Phe Asn Trp Tyr Val Asp Gly Val Glu
 50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys Gly Gly Gly Ser Gly Gly Gly Gly Ser Gly Gly
225                 230                 235                 240

Gly Gly Ser Leu Arg Ser Phe Gly Cys Arg Phe Gly Thr Cys Thr Val
                245                 250                 255

Gln Lys Leu Ala His Gln Ile Tyr Gln Phe Thr Asp Lys Asp Lys Asp
            260                 265                 270

Asn Val Ala Pro Arg Ser Lys Ile Ser Pro Gln Gly Tyr Gly
        275                 280                 285

<210> SEQ ID NO 36
<211> LENGTH: 861
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(861)

<400> SEQUENCE: 36 atg gac aaa act cac aca tgc cca ccg tgc cca gca cct gaa ctc ctg    48
Met Asp Lys Thr His Thr Cys Pro Pro Cys Pro Ala Pro Glu Leu Leu
  1               5                  10                  15 ggg gga ccg tca gtc ttc ctc ttc ccc cca aaa ccc aag gac acc ctc    96
Gly Gly Pro Ser Val Phe Leu Phe Pro Pro Lys Pro Lys Asp Thr Leu
             20                  25                  30 atg atc tcc cgg acc cct gag gtc aca tgc gtg gtg gtg gac gtg agc   144
Met Ile Ser Arg Thr Pro Glu Val Thr Cys Val Val Val Asp Val Ser
         35                  40                  45 cac gaa gac cct gag gtc aag ttc aac tgg tac gtg gac ggc gtg gag   192
His Glu Asp Pro Glu Val Lys Phe Asn Trp Tyr Val Asp Gly Val Glu
     50                  55                  60 gtg cat aat gcc aag aca aag ccg cgg gag gag cag tac aac agc acg   240
Val His Asn Ala Lys Thr Lys Pro Arg Glu Glu Gln Tyr Asn Ser Thr
 65                  70                  75                  80
```

| | |
|---|---|
| tac cgt gtg gtc agc gtc ctc acc gtc ctg cac cag gac tgg ctg aat<br>Tyr Arg Val Val Ser Val Leu Thr Val Leu His Gln Asp Trp Leu Asn<br>                  85                    90                  95 | 288 |
| ggc aag gag tac aag tgc aag gtc tcc aac aaa gcc ctc cca gcc ccc<br>Gly Lys Glu Tyr Lys Cys Lys Val Ser Asn Lys Ala Leu Pro Ala Pro<br>        100                    105                110 | 336 |
| atc gag aaa acc atc tcc aaa gcc aaa ggg cag ccc cga gaa cca cag<br>Ile Glu Lys Thr Ile Ser Lys Ala Lys Gly Gln Pro Arg Glu Pro Gln<br>115                    120                125 | 384 |
| gtg tac acc ctg ccc cca tcc cgg gag gag atg acc aag aac cag gtc<br>Val Tyr Thr Leu Pro Pro Ser Arg Glu Glu Met Thr Lys Asn Gln Val<br>        130                    135                140 | 432 |
| agc ctg acc tgc ctg gtc aaa ggc ttc tat ccc agc gac atc gcc gtg<br>Ser Leu Thr Cys Leu Val Lys Gly Phe Tyr Pro Ser Asp Ile Ala Val<br>145                    150                155                160 | 480 |
| gag tgg gag agc aat ggg cag ccg gag aac aac tac aag acc acg cct<br>Glu Trp Glu Ser Asn Gly Gln Pro Glu Asn Asn Tyr Lys Thr Thr Pro<br>                165                    170                175 | 528 |
| ccc gtg ctg gac tcc gac ggc tcc ttc ttc ctc tac agc aag ctc acc<br>Pro Val Leu Asp Ser Asp Gly Ser Phe Phe Leu Tyr Ser Lys Leu Thr<br>        180                    185                190 | 576 |
| gtg gac aag agc agg tgg cag cag ggg aac gtc ttc tca tgc tcc gtg<br>Val Asp Lys Ser Arg Trp Gln Gln Gly Asn Val Phe Ser Cys Ser Val<br>195                    200                205 | 624 |
| atg cat gag gct ctg cac aac cac tac acg cag aag agc ctc tcc ctg<br>Met His Glu Ala Leu His Asn His Tyr Thr Gln Lys Ser Leu Ser Leu<br>        210                    215                220 | 672 |
| tct ccg ggt aaa gga gga gga tca gga gga gga tca gga gga<br>Ser Pro Gly Lys Gly Gly Gly Ser Gly Gly Gly Ser Gly Gly<br>225                    230                235                240 | 720 |
| gga gga aag ctc cga tcg ttt ggc tgc cgc ttc ggg acg tgc acg gtg<br>Gly Gly Lys Leu Arg Ser Phe Gly Cys Arg Phe Gly Thr Cys Thr Val<br>                245                    250                255 | 768 |
| cag aag ctg gca cac cag atc tac cag ttc aca gat aag gac aag gac<br>Gln Lys Leu Ala His Gln Ile Tyr Gln Phe Thr Asp Lys Asp Lys Asp<br>        260                    265                270 | 816 |
| aac gtc gcc ccc agg agc aag atc agc ccc cag ggc tac ggc tga<br>Asn Val Ala Pro Arg Ser Lys Ile Ser Pro Gln Gly Tyr Gly<br>275                    280                285 | 861 |

<210> SEQ ID NO 37
<211> LENGTH: 286
<212> TYPE: PRT
<213> ORGANISM: Artificial
<220> FEATURE:
<223> OTHER INFORMATION: Synthetic Construct

<400> SEQUENCE: 37

Met Asp Lys Thr His Thr Cys Pro Pro Cys Pro Ala Pro Glu Leu Leu
1                  5                    10                  15

Gly Gly Pro Ser Val Phe Leu Phe Pro Pro Lys Pro Lys Asp Thr Leu
                20                    25                  30

Met Ile Ser Arg Thr Pro Glu Val Thr Cys Val Val Val Asp Val Ser
                  35                    40                  45

His Glu Asp Pro Glu Val Lys Phe Asn Trp Tyr Val Asp Gly Val Glu
        50                    55                  60

Val His Asn Ala Lys Thr Lys Pro Arg Glu Glu Gln Tyr Asn Ser Thr
65                  70                    75                  80

Tyr Arg Val Val Ser Val Leu Thr Val Leu His Gln Asp Trp Leu Asn

|  |  |  | 85 |  |  |  |  | 90 |  |  |  |  | 95 |  |  |
|---|---|---|---|---|---|---|---|---|---|---|---|---|---|---|---|

Gly Lys Glu Tyr Lys Cys Lys Val Ser Asn Lys Ala Leu Pro Ala Pro
           100               105           110

Ile Glu Lys Thr Ile Ser Lys Ala Lys Gly Gln Pro Arg Glu Pro Gln
    115               120              125

Val Tyr Thr Leu Pro Pro Ser Arg Glu Glu Met Thr Lys Asn Gln Val
 130               135              140

Ser Leu Thr Cys Leu Val Lys Gly Phe Tyr Pro Ser Asp Ile Ala Val
145              150              155           160

Glu Trp Glu Ser Asn Gly Gln Pro Glu Asn Asn Tyr Lys Thr Thr Pro
           165              170           175

Pro Val Leu Asp Ser Asp Gly Ser Phe Phe Leu Tyr Ser Lys Leu Thr
        180             185              190

Val Asp Lys Ser Arg Trp Gln Gln Gly Asn Val Phe Ser Cys Ser Val
    195               200              205

Met His Glu Ala Leu His Asn His Tyr Thr Gln Lys Ser Leu Ser Leu
 210               215              220

Ser Pro Gly Lys Gly Gly Gly Ser Gly Gly Gly Ser Gly Gly Gly Ser
225              230              235           240

Gly Gly Lys Leu Arg Ser Phe Gly Cys Arg Phe Gly Thr Cys Thr Val
           245              250           255

Gln Lys Leu Ala His Gln Ile Tyr Gln Phe Thr Asp Lys Asp Lys Asp
        260             265              270

Asn Val Ala Pro Arg Ser Lys Ile Ser Pro Gln Gly Tyr Gly
    275               280              285

```
<210> SEQ ID NO 38
<211> LENGTH: 846
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(846)

<400> SEQUENCE: 38
```

| atg gac aaa act cac aca tgc cca ccg tgc cca gca cct gaa ctc ctg | 48 |
|---|---|
| Met Asp Lys Thr His Thr Cys Pro Pro Cys Pro Ala Pro Glu Leu Leu | |
| 1             5                  10              15 | |
| ggg gga ccg tca gtc ttc ctc ttc ccc cca aaa ccc aag gac acc ctc | 96 |
| Gly Gly Pro Ser Val Phe Leu Phe Pro Pro Lys Pro Lys Asp Thr Leu | |
|            20               25             30 | |
| atg atc tcc cgg acc cct gag gtc aca tgc gtg gtg gtg gac gtg agc | 144 |
| Met Ile Ser Arg Thr Pro Glu Val Thr Cys Val Val Val Asp Val Ser | |
|         35               40              45 | |
| cac gaa gac cct gag gtc aag ttc aac tgg tac gtg gac ggc gtg gag | 192 |
| His Glu Asp Pro Glu Val Lys Phe Asn Trp Tyr Val Asp Gly Val Glu | |
|     50               55              60 | |
| gtg cat aat gcc aag aca aag ccg cgg gag gag cag tac aac agc acg | 240 |
| Val His Asn Ala Lys Thr Lys Pro Arg Glu Glu Gln Tyr Asn Ser Thr | |
| 65              70              75           80 | |
| tac cgt gtg gtc agc gtc ctc acc gtc ctg cac cag gac tgg ctg aat | 288 |
| Tyr Arg Val Val Ser Val Leu Thr Val Leu His Gln Asp Trp Leu Asn | |
|                85              90           95 | |
| ggc aag gag tac aag tgc aag gtc tcc aac aaa gcc ctc cca gcc ccc | 336 |
| Gly Lys Glu Tyr Lys Cys Lys Val Ser Asn Lys Ala Leu Pro Ala Pro | |
|            100               105           110 | |

```
atc gag aaa acc atc tcc aaa gcc aaa ggg cag ccc cga gaa cca cag      384
Ile Glu Lys Thr Ile Ser Lys Ala Lys Gly Gln Pro Arg Glu Pro Gln
            115                 120                 125 gtg tac acc ctg ccc cca tcc cgg gag gag atg acc aag aac cag gtc      432
Val Tyr Thr Leu Pro Pro Ser Arg Glu Glu Met Thr Lys Asn Gln Val
        130                 135                 140 agc ctg acc tgc ctg gtc aaa ggc ttc tat ccc agc gac atc gcc gtg      480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct      528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc      576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg      624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg      672
Met His Glu Ala Leu His Asn His Tyr Thr Gln Lys Ser Leu Ser Leu
210                 215                 220 tct ccg ggt aaa tac cgc cag agc atg aac aac ttc cag ggc ctc cga      720
Ser Pro Gly Lys Tyr Arg Gln Ser Met Asn Asn Phe Gln Gly Leu Arg
225                 230                 235                 240 tcg ttt ggc tgc cgc ttc ggg acg tgc acg gtg cag aag ctg gca cac      768
Ser Phe Gly Cys Arg Phe Gly Thr Cys Thr Val Gln Lys Leu Ala His
                245                 250                 255 cag atc tac cag ttc aca gat aag gac aag gac aac gtc gcc ccc agg      816
Gln Ile Tyr Gln Phe Thr Asp Lys Asp Lys Asp Asn Val Ala Pro Arg
            260                 265                 270 agc aag atc agc ccc cag ggc tac ggc tga                              846
Ser Lys Ile Ser Pro Gln Gly Tyr Gly
        275                 280

<210> SEQ ID NO 39
<211> LENGTH: 281
<212> TYPE: PRT
<213> ORGANISM: Artificial
<220> FEATURE:
<223> OTHER INFORMATION: Synthetic Construct

<400> SEQUENCE: 39

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Glu Glu Met Thr Lys Asn Gln Val
```

```
                130                 135                 140
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
                195                 200                 205

Met His Glu Ala Leu His Asn His Tyr Thr Gln Lys Ser Leu Ser Leu
                210                 215                 220

Ser Pro Gly Lys Tyr Arg Gln Ser Met Asn Asn Phe Gln Gly Leu Arg
225                 230                 235                 240

Ser Phe Gly Cys Arg Phe Gly Thr Cys Thr Val Gln Lys Leu Ala His
                245                 250                 255

Gln Ile Tyr Gln Phe Thr Asp Lys Asp Lys Asp Asn Val Ala Pro Arg
                260                 265                 270

Ser Lys Ile Ser Pro Gln Gly Tyr Gly
            275                 280

<210> SEQ ID NO 40
<211> LENGTH: 867
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(867)

<400> SEQUENCE: 40 atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc      96
Ser Val Phe Leu Phe Pro Pro Lys Pro Lys Asp Thr Leu Met Ile Ser
                20                  25                  30 cgg acc cct gag gtc acg tgc gtg gtg gtg gac gtg agc cag gaa gac     144
Arg Thr Pro Glu Val Thr Cys Val Val Val Asp Val Ser Gln Glu Asp
            35                  40                  45 ccc gag gtc cag ttc aac tgg tac gtg gat ggc gtg gag gtg cat aat     192
Pro Glu Val Gln Phe Asn Trp Tyr Val Asp Gly Val Glu Val His Asn
        50                  55                  60 gcc aag aca aag ccg cgg gag gag cag ttc aac agc acg tac cgt gtg     240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag     288
Val Ser Val Leu Thr Val Leu His Gln Asp Trp Leu Asn Gly Lys Glu
                85                  90                  95 tac aag tgc aag gtc tcc aac aaa ggc ctc ccg tcc tcc atc gag aaa     336
Tyr Lys Cys Lys Val Ser Asn Lys Gly Leu Pro Ser Ser Ile Glu Lys
                100                 105                 110 acc atc tcc aaa gcc aaa ggg cag ccc cga gag cca cag gtg tac acc     384
Thr Ile Ser Lys Ala Lys Gly Gln Pro Arg Glu Pro Gln Val Tyr Thr
            115                 120                 125 ctg ccc cca tcc cag gag gag atg acc aag aac cag gtc agc ctg acc     432
Leu Pro Pro Ser Gln Glu Glu Met Thr Lys Asn Gln Val Ser Leu Thr
        130                 135                 140 tgc ctg gtc aaa ggc ttc tac ccc agc gac atc gcc gtg gag tgg gag     480
Cys Leu Val Lys Gly Phe Tyr Pro Ser Asp Ile Ala Val Glu Trp Glu
```

```
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg    528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag    576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag    624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt    672
Ala Leu His Asn His Tyr Thr Gln Lys Ser Leu Ser Leu Ser Pro Gly
    210                 215                 220 aaa gga gga gga tca gga gga gga gga tca gga gga gga gga tca        720
Lys Gly Gly Gly Ser Gly Gly Gly Gly Ser Gly Gly Gly Gly Ser
225                 230                 235                 240 aac aac ttc cag ggc ctc cgg agc ttt ggc tgc cgc ttc ggg acg tgc    768
Asn Asn Phe Gln Gly Leu Arg Ser Phe Gly Cys Arg Phe Gly Thr Cys
                245                 250                 255 acg gtg cag aag ctg gca cac cag atc tac cag ttc aca gat aag gac    816
Thr Val Gln Lys Leu Ala His Gln Ile Tyr Gln Phe Thr Asp Lys Asp
            260                 265                 270 aag gac aac gtc gcc ccc agg agc aag atc agc ccc cag ggc tac ggc    864
Lys Asp Asn Val Ala Pro Arg Ser Lys Ile Ser Pro Gln Gly Tyr Gly
        275                 280                 285 tga                                                                867
```

```
<210> SEQ ID NO 41
<211> LENGTH: 288
<212> TYPE: PRT
<213> ORGANISM: Artificial
<220> FEATURE:
<223> OTHER INFORMATION: Synthetic Construct

<400> SEQUENCE: 41

Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser Gln Glu Asp
            35                  40                  45

Pro Glu Val Gln Phe Asn Trp Tyr Val Asp Gly Val Glu Val His Asn
        50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175
```

```
Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Gly Ser Gly Gly Gly Ser Gly Gly Gly Ser
225                 230                 235                 240

Asn Asn Phe Gln Gly Leu Arg Ser Phe Gly Cys Arg Phe Gly Thr Cys
                245                 250                 255

Thr Val Gln Lys Leu Ala His Gln Ile Tyr Gln Phe Thr Asp Lys Asp
            260                 265                 270

Lys Asp Asn Val Ala Pro Arg Ser Lys Ile Ser Pro Gln Gly Tyr Gly
        275                 280                 285

<210> SEQ ID NO 42
<211> LENGTH: 867
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(867)

<400> SEQUENCE: 42 atg ccc cca tgc cca tca tgc cca gca cct gag ttc ctg ggg gga cca    48
Met Pro Pro Cys Pro Ser Cys Pro Ala Pro Glu Phe Leu Gly Gly Pro
1               5                  10                  15 tca gtc ttc ctg ttc ccc cca aaa ccc aag gac act ctc atg atc tcc    96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac   144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat   192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg   240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag   288
Val Ser Val Leu Thr Val Leu His Gln Asp Trp Leu Asn Gly Lys Glu
                85                  90                  95 tac aag tgc aag gtc tcc aac aaa ggc ctc ccg tcc tcc atc gag aaa   336
Tyr Lys Cys Lys Val Ser Asn Lys Gly Leu Pro Ser Ser Ile Glu Lys
            100                 105                 110 acc atc tcc aaa gcc aaa ggg cag ccc cga gag cca cag gtg tac acc   384
Thr Ile Ser Lys Ala Lys Gly Gln Pro Arg Glu Pro Gln Val Tyr Thr
        115                 120                 125 ctg ccc cca tcc cag gag gag atg acc aag aac cag gtc agc ctg acc   432
Leu Pro Pro Ser Gln Glu Glu Met Thr Lys Asn Gln Val Ser Leu Thr
    130                 135                 140 tgc ctg gtc aaa ggc ttc tac ccc agc gac atc gcc gtg gag tgg gag   480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg   528
Ser Asn Gly Gln Pro Glu Asn Asn Tyr Lys Thr Thr Pro Pro Val Leu
                165                 170                 175
```

```
gac tcc gac ggc tcc ttc ttc ctc tac agc aag cta acc gtg gac aag      576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag      624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt      672
Ala Leu His Asn His Tyr Thr Gln Lys Ser Leu Ser Leu Ser Pro Gly
    210                 215                 220 aaa gga gga gga tca gga gga gga tca gga gga gga aag                  720
Lys Gly Gly Gly Ser Gly Gly Gly Ser Gly Gly Gly Lys
225             230                 235             240 aac aac ttc cag ggc ctc cgg agc ttt ggc tgc cgc ttc ggg acg tgc      768
Asn Asn Phe Gln Gly Leu Arg Ser Phe Gly Cys Arg Phe Gly Thr Cys
                245                 250                 255 acg gtg cag aag ctg gca cac cag atc tac cag ttc aca gat aag gac      816
Thr Val Gln Lys Leu Ala His Gln Ile Tyr Gln Phe Thr Asp Lys Asp
            260                 265                 270 aag gac aac gtc gcc ccc agg agc aag atc agc ccc cag ggc tac ggc      864
Lys Asp Asn Val Ala Pro Arg Ser Lys Ile Ser Pro Gln Gly Tyr Gly
        275                 280                 285 tga                                                                   867

<210> SEQ ID NO 43
<211> LENGTH: 288
<212> TYPE: PRT
<213> ORGANISM: Artificial
<220> FEATURE:
<223> OTHER INFORMATION: Synthetic Construct

<400> SEQUENCE: 43

Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205
```

```
Ala Leu His Asn His Tyr Thr Gln Lys Ser Leu Ser Leu Ser Pro Gly
    210                 215                 220
Lys Gly Gly Gly Ser Gly Gly Gly Ser Gly Gly Gly Lys
225                 230                 235                 240
Asn Asn Phe Gln Gly Leu Arg Ser Phe Gly Cys Arg Phe Gly Thr Cys
                245                 250                 255
Thr Val Gln Lys Leu Ala His Gln Ile Tyr Gln Phe Thr Asp Lys Asp
                260                 265                 270
Lys Asp Asn Val Ala Pro Arg Ser Lys Ile Ser Pro Gln Gly Tyr Gly
                275                 280                 285
```

<210> SEQ ID NO 44
<211> LENGTH: 852
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(852)

<400> SEQUENCE: 44

```
atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc      96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac     144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat     192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg     240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag     288
Val Ser Val Leu Thr Val Leu His Gln Asp Trp Leu Asn Gly Lys Glu
                85                  90                  95 tac aag tgc aag gtc tcc aac aaa ggc ctc ccg tcc tcc atc gag aaa     336
Tyr Lys Cys Lys Val Ser Asn Lys Gly Leu Pro Ser Ser Ile Glu Lys
            100                 105                 110 acc atc tcc aaa gcc aaa ggg cag ccc cga gag cca cag gtg tac acc     384
Thr Ile Ser Lys Ala Lys Gly Gln Pro Arg Glu Pro Gln Val Tyr Thr
        115                 120                 125 ctg ccc cca tcc cag gag gag atg acc aag aac cag gtc agc ctg acc     432
Leu Pro Pro Ser Gln Glu Glu Met Thr Lys Asn Gln Val Ser Leu Thr
    130                 135                 140 tgc ctg gtc aaa ggc ttc tac ccc agc gac atc gcc gtg gag tgg gag     480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg     528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag     576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag     624
Ser Arg Trp Gln Glu Gly Asn Val Phe Ser Cys Ser Val Met His Glu
        195                 200                 205
```

```
gct ctg cac aac cac tac aca cag aag agc ctc tcc ctg tct ccg ggt        672
Ala Leu His Asn His Tyr Thr Gln Lys Ser Leu Ser Leu Ser Pro Gly
    210             215                 220 aaa gga gga gga tca gga gga gga tca gga gga gga tca                    720
Lys Gly Gly Gly Ser Gly Gly Gly Ser Gly Gly Gly Ser
225             230             235             240 ctc cgg agc ttt ggc tgc cgc ttc ggg acg tgc acg gtg cag aag ctg        768
Leu Arg Ser Phe Gly Cys Arg Phe Gly Thr Cys Thr Val Gln Lys Leu
                245             250             255 gca cac cag atc tac cag ttc aca gat aag gac aag gac aac gtc gcc        816
Ala His Gln Ile Tyr Gln Phe Thr Asp Lys Asp Lys Asp Asn Val Ala
        260             265             270 ccc agg agc aag atc agc ccc cag ggc tac ggc tga                        852
Pro Arg Ser Lys Ile Ser Pro Gln Gly Tyr Gly
    275             280
```

<210> SEQ ID NO 45
<211> LENGTH: 283
<212> TYPE: PRT
<213> ORGANISM: Artificial
<220> FEATURE:
<223> OTHER INFORMATION: Synthetic Construct

<400> SEQUENCE: 45

```
Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Gly Ser Gly Gly Gly Ser Gly Gly Gly Ser
225                 230                 235                 240

Leu Arg Ser Phe Gly Cys Arg Phe Gly Thr Cys Thr Val Gln Lys Leu
                245                 250                 255
```

```
                Ala His Gln Ile Tyr Gln Phe Thr Asp Lys Asp Lys Asp Asn Val Ala
                                260                 265                 270

Pro Arg Ser Lys Ile Ser Pro Gln Gly Tyr Gly
                        275                 280

<210> SEQ ID NO 46
<211> LENGTH: 852
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(852)

<400> SEQUENCE: 46 atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc      96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac     144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat     192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg     240
Ala Lys Thr Lys Pro Arg Glu Glu Gln Phe Asn Ser Thr Tyr Arg Val
65                  70                  75                  80 gtc agc gtc ctc acc gtc ctg cac cag gac tgg ctg aac ggc aag gag     288
Val Ser Val Leu Thr Val Leu His Gln Asp Trp Leu Asn Gly Lys Glu
                85                  90                  95 tac aag tgc aag gtc tcc aac aaa ggc ctc ccg tcc tcc atc gag aaa     336
Tyr Lys Cys Lys Val Ser Asn Lys Gly Leu Pro Ser Ser Ile Glu Lys
            100                 105                 110 acc atc tcc aaa gcc aaa ggg cag ccc cga gag cca cag gtg tac acc     384
Thr Ile Ser Lys Ala Lys Gly Gln Pro Arg Glu Pro Gln Val Tyr Thr
        115                 120                 125 ctg ccc cca tcc cag gag gag atg acc aag aac cag gtc agc ctg acc     432
Leu Pro Pro Ser Gln Glu Glu Met Thr Lys Asn Gln Val Ser Leu Thr
    130                 135                 140 tgc ctg gtc aaa ggc ttc tac ccc agc gac atc gcc gtg gag tgg gag     480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg     528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag     576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag     624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt     672
Ala Leu His Asn His Tyr Thr Gln Lys Ser Leu Ser Leu Ser Pro Gly
    210                 215                 220 aaa gga gga gga gga tca gga gga gga gga tca gga gga gga gga aag     720
Lys Gly Gly Gly Gly Ser Gly Gly Gly Gly Ser Gly Gly Gly Gly Lys
225                 230                 235                 240
```

```
ctc cgg agc ttt ggc tgc cgc ttc ggg acg tgc acg gtg cag aag ctg      768
Leu Arg Ser Phe Gly Cys Arg Phe Gly Thr Cys Thr Val Gln Lys Leu
            245                 250                 255 gca cac cag atc tac cag ttc aca gat aag gac aag gac aac gtc gcc      816
Ala His Gln Ile Tyr Gln Phe Thr Asp Lys Asp Lys Asp Asn Val Ala
            260                 265                 270 ccc agg agc aag atc agc ccc cag ggc tac ggc tga                      852
Pro Arg Ser Lys Ile Ser Pro Gln Gly Tyr Gly
            275                 280
```

<210> SEQ ID NO 47
<211> LENGTH: 283
<212> TYPE: PRT
<213> ORGANISM: Artificial
<220> FEATURE:
<223> OTHER INFORMATION: Synthetic Construct

<400> SEQUENCE: 47

```
Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Gly Gly Gly Ser Gly Gly Gly Ser Gly Gly Gly Lys
225                 230                 235                 240

Leu Arg Ser Phe Gly Cys Arg Phe Gly Thr Cys Thr Val Gln Lys Leu
                245                 250                 255

Ala His Gln Ile Tyr Gln Phe Thr Asp Lys Asp Lys Asp Asn Val Ala
            260                 265                 270

Pro Arg Ser Lys Ile Ser Pro Gln Gly Tyr Gly
        275                 280
```

<210> SEQ ID NO 48
<211> LENGTH: 837

```
<212> TYPE: DNA
<213> ORGANISM: Artificial
<220> FEATURE:
<223> OTHER INFORMATION: Designed peptide
<220> FEATURE:
<221> NAME/KEY: CDS
<222> LOCATION: (1)..(837)

<400> SEQUENCE: 48 atg ccc cca tgc cca tca tgc cca gca cct gag ttc ctg ggg gga cca      48
Met Pro Pro Cys Pro Ser Cys Pro Ala Pro Glu Phe Leu Gly Gly Pro
1               5                   10                  15 tca gtc ttc ctg ttc ccc cca aaa ccc aag gac act ctc atg atc tcc      96
Ser Val Phe Leu Phe Pro Pro Lys Pro Lys Asp Thr Leu Met Ile Ser
            20                  25                  30 cgg acc cct gag gtc acg tgc gtg gtg gtg gac gtg agc cag gaa gac     144
Arg Thr Pro Glu Val Thr Cys Val Val Val Asp Val Ser Gln Glu Asp
        35                  40                  45 ccc gag gtc cag ttc aac tgg tac gtg gat ggc gtg gag gtg cat aat     192
Pro Glu Val Gln Phe Asn Trp Tyr Val Asp Gly Val Glu Val His Asn
    50                  55                  60 gcc aag aca aag ccg cgg gag gag cag ttc aac agc acg tac cgt gtg     240
Ala Lys Thr Lys Pro Arg Glu Glu Gln Phe Asn Ser Thr Tyr Arg Val
65              70                  75                  80 gtc agc gtc ctc acc gtc ctg cac cag gac tgg ctg aac ggc aag gag     288
Val Ser Val Leu Thr Val Leu His Gln Asp Trp Leu Asn Gly Lys Glu
            85                  90                  95 tac aag tgc aag gtc tcc aac aaa ggc ctc ccg tcc tcc atc gag aaa     336
Tyr Lys Cys Lys Val Ser Asn Lys Gly Leu Pro Ser Ser Ile Glu Lys
        100                 105                 110 acc atc tcc aaa gcc aaa ggg cag ccc cga gag cca cag gtg tac acc     384
Thr Ile Ser Lys Ala Lys Gly Gln Pro Arg Glu Pro Gln Val Tyr Thr
    115                 120                 125 ctg ccc cca tcc cag gag gag atg acc aag aac cag gtc agc ctg acc     432
Leu Pro Pro Ser Gln Glu Glu Met Thr Lys Asn Gln Val Ser Leu Thr
130                 135                 140 tgc ctg gtc aaa ggc ttc tac ccc agc gac atc gcc gtg gag tgg gag     480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc gtg ctg     528
Ser Asn Gly Gln Pro Glu Asn Asn Tyr Lys Thr Thr Pro Pro Val Leu
                165                 170                 175 gac tcc gac ggc tcc ttc ttc ctc tac agc aag cta acc gtg gac aag     576
Asp Ser Asp Gly Ser Phe Phe Leu Tyr Ser Lys Leu Thr Val Asp Lys
            180                 185                 190 agc agg tgg cag gag ggg aat gtc ttc tca tgc tcc gtg atg cat gag     624
Ser Arg Trp Gln Glu Gly Asn Val Phe Ser Cys Ser Val Met His Glu
        195                 200                 205 gct ctg cac aac cac tac aca cag aag agc ctc tcc ctg tct ccg ggt     672
Ala Leu His Asn His Tyr Thr Gln Lys Ser Leu Ser Leu Ser Pro Gly
    210                 215                 220 aaa tac cgc cag agc atg aac aac ttc cag ggc ctc cgg agc ttt ggc     720
Lys Tyr Arg Gln Ser Met Asn Asn Phe Gln Gly Leu Arg Ser Phe Gly
225                 230                 235                 240 tgc cgc ttc ggg acg tgc acg gtg cag aag ctg gca cac cag atc tac     768
Cys Arg Phe Gly Thr Cys Thr Val Gln Lys Leu Ala His Gln Ile Tyr
                245                 250                 255 cag ttc aca gat aag gac aag gac aac gtc gcc ccc agg agc aag atc     816
Gln Phe Thr Asp Lys Asp Lys Asp Asn Val Ala Pro Arg Ser Lys Ile
            260                 265                 270 agc ccc cag ggc tac ggc tga                                         837
Ser Pro Gln Gly Tyr Gly
```

```
Ser Pro Gln Gly Tyr Gly
        275

<210> SEQ ID NO 49
<211> LENGTH: 278
<212> TYPE: PRT
<213> ORGANISM: Artificial
<220> FEATURE:
<223> OTHER INFORMATION: Synthetic Construct

<400> SEQUENCE: 49

Met Pro Pro Cys Pro Ser Cys Pro Ala Pro Glu Phe Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser Gln Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Gln Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Glu Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys Tyr Arg Gln Ser Met Asn Asn Phe Gln Gly Leu Arg Ser Phe Gly
225                 230                 235                 240

Cys Arg Phe Gly Thr Cys Thr Val Gln Lys Leu Ala His Gln Ile Tyr
                245                 250                 255

Gln Phe Thr Asp Lys Asp Lys Asp Asn Val Ala Pro Arg Ser Lys Ile
            260                 265                 270

Ser Pro Gln Gly Tyr Gly
        275
```

LONG-ACTING ADRENOMEDULLIN DERIVATIVE CONJUGATED WITH FC REGION OF IMMUNOGLOBULIN

CROSS-REFERENCE TO RELATED APPLICATIONS

This application is the U.S. National Stage of PCT/JP2018/013075, filed Mar. 29, 2018, which claims priority to JP 2017-064369, filed Mar. 29, 2017.

The instant application contains a Sequence Listing which has been submitted in ASCII format via EFS-WEB and is hereby incorporated by reference in its entirety. Said ASCII copy, created on Sep. 26, 2019, is named sequence.txt and is 117,086 bytes.

TECHNICAL FIELD

The invention relates to long-acting adrenomedullin derivatives.

BACKGROUND ART

Adrenomedullin (hereinafter, also described as "AM") is a bioactive peptide which was isolated and identified from pheochromocytoma in 1993 (Non Patent Literature 1). At the beginning of the discovery, AM was found to exert a strong vasodilatory hypotensive effect. For example, Patent Literature 1 describes a peptide having a blood pressure-lowering effect that comprises the amino acid sequence of human AM.

Subsequent studies revealed that AM exerts diverse pharmacological effects such as a cardiovascular protective effect, an anti-inflammatory effect, an angiogenic effect, and a tissue repair promoting effect. In an effort to apply the pharmacological effects of AM to treatment of disease, administration of AM to patients with different diseases has been attempted. AM is expected to be useful as a therapeutic agent for inflammatory bowel diseases, pulmonary hypertension, peripheral vascular diseases, or acute myocardial infarction, among others.

For example, Patent Literature 2 describes an agent for preventing or treating nonbacterial inflammatory bowel diseases, wherein the agent comprises, as an active ingredient, adrenomedullin or a derivative thereof that has an activity to suppress nonbacterial inflammation, or a salt thereof that has an activity to suppress nonbacterial inflammation.

Patent Literature 3 describes a method for preventing or treating an inflammatory bowel disease for which the use of a steroid preparation, an immunosuppressant, or a biological product is difficult or insufficiently effective in a patient in need of prevention or treatment of the inflammatory bowel disease, the method comprising administering an effective amount of adrenomedullin, a modified form thereof having an activity of suppressing inflammation, or a salt of the adrenomedullin or the modified form having an activity of suppressing inflammation, to the patient.

Structure-activity relationship studies of AM have advanced identification of essential sequences that can contribute bioactivity of AM (Non Patent Literatures 2 to 9).

Peptides are generally known to have a short half-life due to a metabolism in a living body (such as in blood). Therefore, in the case of using peptides as active ingredients in medicaments, forms of peptide derivatives in which other groups are linked to the peptides can prolong half-life in a living body and improve pharmacokinetics, in some cases.

For example, Patent Literature 4 describes a biologically active intermedin peptide or adrenomedullin peptide characterized by having a serum half-life exceeding 1.5 hours. The literature states that an alkyl group and a peptide moiety are linked via an amide bond.

Patent Literature 5 describes an AM derivative linked to a polyethylene glycol (hereinafter, also described as "PEG") group via the phenolic hydroxy group of Tyr' of AM.

Patent Literature 6 describes a method comprising reacting PEG-aldehyde with a free amino group of a peptide to produce a peptide derivative having the PEG group linked to the free amino group of the peptide. The literature describes AM as the peptide.

Non Patent Literature 10 describes an AM derivative in which a PEG group is linked to the N-terminal α-amino group of AM via an amide bond. The literature states that blood half-life of the AM derivative having the linked PEG group was prolonged.

Patent Literature 7 describes a fusion protein comprising: a first segment containing a sequence of a first bioactive peptide or protein, the first segment being positioned at the amino terminus of the fusion protein; and a second segment containing a sequence of a second bioactive protein or peptide, the second segment being positioned at the carboxyl terminus of the fusion protein, wherein the first and second segments are covalently bound to each other so as to function. The literature states that the fusion protein may further comprise a linker segment, such as an Fc fragment of an immunoglobulin or a functional equivalent thereof, binding to the first segment and the second segment. The literature makes no mention about adrenomedullin.

Patent Literature 8 describes an engineered polypeptide comprising an albumin binding domain polypeptide (ABD) and a first peptide hormone domain (HD1) selected from leptin, a leptin analog, or an active fragment thereof. The literature describes an Fc protein as a water-soluble polymer moiety contained in HD1. The literature states that the engineered polypeptide has a favorable duration of action. The literature lists amylin such as adrenomedullin, or an analog thereof as an example of a drug that may be administered in combination with the engineered polypeptide.

Patent Literature 9 describes an Fc-interferon-β fusion protein that improves folding and decreases aggregation, comprising: (i) an immunoglobulin Fc region; and (ii) an interferon-β protein linked to the carboxy terminus of the immunoglobulin Fc region through a peptide bond or a peptide linker sequence. The literature states that the fusion protein is capable of improving blood half-life of interferon-β. The literature makes no mention about adrenomedullin.

CITATION LIST

Patent Literature

Patent Literature 1: JP Patent No. 2774769
Patent Literature 2: JP Patent No. 4830093
Patent Literature 3: International Publication No. WO 2012/096411
Patent Literature 4: International Publication No. WO 2012/138867
Patent Literature 5: International Publication No. WO 2013/064508
Patent Literature 6: U.S. Patent Publication. No. US 2009/0252703
Patent Literature 7: JP Patent Publication (Kohyo) No. 2009-510999A Patent Literature 8: JP Patent Publication (Kohyo) No. 2014-528917A Patent Literature 9: JP Patent No. 4808709

Non Patent Literature

Non Patent Literature 1: Kitamura K, Kangawa K, Kawamoto M, Ichiki Y, Nakamura S, Matsuo H, Eto T. Adrenomedullin: a novel hypotensive peptide isolated from human pheochromocytoma. Biochem Biophys Res Commun, 30 Apr. 1993, Volume 192, Issue 2, pp. 553-560.

Non Patent Literature 2: Belloni, A. S. et al., Structure-activity relationships of adrenomedullin in the adrenal gland. Endocr Res, 1998, Volume 24, Issue 3-4, p. 729-30.

Non Patent Literature 3: Champion, H. C. et al., Catecholamine release mediates pressor effects of adrenomedullin-(15-22) in the rat. Hypertension, 1996, Volume 28, Issue 6, p. 1041-6.

Non Patent Literature 4: Champion, H. C., G. G. Nussdorfer, and P. J. Kadowitz, Structure-activity relationships of adrenomedullin in the circulation and adrenal gland. Regul Pept, 1999, Volume 85, Issue 1, p. 1-8.

Non Patent Literature 5: Eguchi, S. et al., Structure-activity relationship of adrenomedullin, a novel vasodilatory peptide, in cultured rat vascular smooth muscle cells. Endocrinology, 1994, Volume 135, Issue 6, p. 2454-8.

Non Patent Literature 6: Garcia, M. A. et al., Synthesis, biological evaluation, and three-dimensional quantitative structure-activity relationship study of small-molecule positive modulators of adrenomedullin. J Med Chem, 2005, Volume 48, Issue 12, p. 4068-75.

Non Patent Literature 7: Mitsuda, Y. et al., Large-scale production of functional human adrenomedullin: expression, cleavage, amidation, and purification. Protein Expr Purif, 2002, Volume 25, Issue 3, p. 448-55.

Non Patent Literature 8: Roldos, V. et al., Small-molecule negative modulators of adrenomedullin: design, synthesis, and 3D-QSAR study. Chem Med Chem, 2008, Volume 3, Issue 9, p. 1345-55.

Non Patent Literature 9: Watanabe, T. X. et al., Vasopressor activities of N-terminal fragments of adrenomedullin in anesthetized rat. Biochem Biophys Res Commun, 1996, Volume 219, Issue 1, p. 59-63.

Non Patent Literature 10: Kubo, K et al., Biological properties of adrenomedullin conjugated with polyethylene glycol. Peptides, 2014, Volume 57, p. 118-21.

Non Patent Literature 11: Kato, J., Kitamura, K. Bench-to-bedside pharmacology of adrenomedullin. European Journal of Pharmacology, 2015, Volume 764, p. 140-148.

SUMMARY OF INVENTION

Technical Problem

As described above, AM derivatives in which other groups such as a PEG group are linked to AM are known in order to improve the pharmacokinetics of AM from the viewpoint of improvement in sustainability in a living body. However, known AM derivatives are susceptible to improvement. For example, in the case of linking a relatively large group such as a PEG group to a relatively small peptide such as AM, various properties of the resulting AM derivative may vary largely depending on the molecular weight of the PEG group. As in the AM derivative described in Patent Literature 5, in the case of linking other groups to the side chain of an amino acid residue of AM, the conformation of the AM moiety may be changed to reduce the affinity for an AM receptor recognizing AM. In such a case, pharmacological effects as AM of the resulting AM derivative may be reduced.

AM has a strong vasodilatory effect, in addition to pharmacological effects such as a cardiovascular protective effect, an anti-inflammatory effect, an angiogenic effect, and a tissue repair promoting effect. This strong vasodilatory effect may cause unwanted side effects such as excessive decreased blood pressure when AM or an AM derivative is administered to subjects. The occurrence of such side effects may become a problem when AM or an AM derivative is used, particularly, in the expectation that pharmacological effects other than a vasodilatory effect are exerted. To avoid generating the problems described above, a medicament comprising adrenomedullin or a derivative thereof as an active ingredient according to a conventional technique is required to be administered to subjects via continuous intravenous infusion in a dose that does not substantially cause unwanted side effects. Such a mode of administration may force subjects to bear an undue burden.

Adrenomedullin derivatives which maintain pharmacological effects of adrenomedullin and have improved sustainability in a living body are expected to be capable of exerting pharmacological effects of adrenomedullin without substantially causing unwanted side effects, even when administered to subjects in a single dose. The invention, therefore, is intended to provide novel adrenomedullin derivatives sustainable for a long period which are capable of substantially suppressing unwanted side effects while maintaining pharmacological effects of adrenomedullin.

Solution to Problem

The present inventors conducted various investigations of means to solve the problems described above. The present inventors have found that linking of the N-terminal α-amino group of adrenomedullin to an Fc region of an immunoglobulin via a linking group of a peptide having a specific amino acid sequence can retain bioactivity at the same level as in the parent compound adrenomedullin. The present inventors have achieved the invention based on the finding described above.

That is to say, a summary of the invention is as the following:

(1) A compound represented by formula (I):

A-L-B          (I)

wherein

A is an Fc region of an immunoglobulin,

B is a peptide moiety derived from adrenomedullin or a modified form thereof with adrenomedullin activity, and L is a linking group comprising a peptide having any given amino acid sequence, or a salt thereof, or a hydrate thereof.

(2) The compound according to the embodiment (1), wherein L is a linking group comprising a peptide having the following amino acid sequence:

```
                              (SEQ ID NO: 22)
GGGGSGGGGSGGGGS;
or
                              (SEQ ID NO: 24)
GGGGSGGGGSGGGGK,
``` the Fc region A is linked to the other moieties through a peptide bond formed by the C-terminal carboxyl group of the Fc region A and the N-terminal α-amino group of the linking group L, and the peptide moiety B is linked to the other moieties through a peptide bond formed by the N-terminal α-amino group of the peptide moiety B and the C-terminal carboxyl group of the linking group L.

(3) The compound according to the embodiment (1) or (2), wherein A is an Fc region of immunoglobulin G1 (IgG1) or an Fc region of immunoglobulin G4 (IgG4).

(4) The compound according to any of the embodiments (1) to (3), wherein the adrenomedullin or the modified form thereof with adrenomedullin activity is a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(iii) the peptide of (ii) wherein the disulfide bond of the peptide is substituted with an ethylene group and the peptide has adrenomedullin activity,
(iv) any peptide of (i) to (iii) wherein the peptide has the amino acid sequence comprising deletion, substitution, or addition of one to fifteen amino acid residues and has adrenomedullin activity,
(v) any peptide of (i) to (iv) wherein the peptide is amidated at the C-terminus thereof, and
(vi) any peptide of (i) to (iv) wherein the peptide has a glycine residue added to the C-terminus thereof.

(5) The compound according to the embodiment (4), wherein the adrenomedullin or the modified form thereof is a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(v) the peptide of (i) or (ii) wherein the peptide is amidated at the C-terminus thereof, and
(vi) the peptide of (i) or (ii) wherein the peptide has a glycine residue added to the C-terminus thereof.

(6) The compound according to any of the embodiments (1) to (4), wherein the adrenomedullin or the modified form thereof is a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 4, or a peptide consisting of the amino acid sequence of SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(g) any peptide of (a) to (f) wherein the disulfide bond of the peptide is substituted with an ethylene group and the peptide has adrenomedullin activity;
(h) any peptide of (a) to (g) wherein the peptide has the amino acid sequence comprising deletion, substitution, or addition of one to fifteen amino acids and has adrenomedullin activity;
(i) any peptide of (a) to (h) wherein the peptide is amidated at the C-terminus thereof; and
(j) any peptide of (a) to (h) wherein the peptide has a glycine residue added to the C-terminus thereof.

(7) The compound according to the embodiment (6), wherein the adrenomedullin or the modified form thereof is a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 4, or a peptide consisting of the amino acid sequence of SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(i) any peptide of (a) to (0 wherein the peptide is amidated at the C-terminus thereof; and
(j) any peptide of (a) to (0 wherein the peptide has a glycine residue added to the C-terminus thereof.

(8) The compound according to any of the embodiments (1) to (4), wherein the compound represented by formula (I) is a peptide selected from the group consisting of:
(E-a-1) a peptide consisting of the amino acid sequence of SEQ ID NO: 15, or a peptide consisting of the amino acid sequence of SEQ ID NO: 15 and having a disulfide bond formed by the cysteine residues at positions 259 and 264;
(E-a-2) a peptide consisting of the amino acid sequence of SEQ ID NO: 17, or a peptide consisting of the amino acid sequence of SEQ ID NO: 17 and having a disulfide bond formed by the cysteine residues at positions 259 and 264;
(E-a-3) a peptide consisting of the amino acid sequence of SEQ ID NO: 19, or a peptide consisting of the amino acid sequence of SEQ ID NO: 19 and having a disulfide bond formed by the cysteine residues at positions 256 and 261;
(E-a-4) a peptide consisting of the amino acid sequence of SEQ ID NO: 21, or a peptide consisting of the amino acid sequence of SEQ ID NO: 21 and having a disulfide bond formed by the cysteine residues at positions 256 and 261;
(E-a-5) a peptide consisting of the amino acid sequence of SEQ ID NO: 31, or a peptide consisting of the amino acid sequence of SEQ ID NO: 31 and having a disulfide bond formed by the cysteine residues at positions 254 and 259;
(E-a-6) a peptide consisting of the amino acid sequence of SEQ ID NO: 33, or a peptide consisting of the amino acid sequence of SEQ ID NO: 33 and having a disulfide bond formed by the cysteine residues at positions 254 and 259;
(E-a-7) a peptide consisting of the amino acid sequence of SEQ ID NO: 35, or a peptide consisting of the amino acid sequence of SEQ ID NO: 35 and having a disulfide bond formed by the cysteine residues at positions 249 and 254;
(E-a-8) a peptide consisting of the amino acid sequence of SEQ ID NO: 37, or a peptide consisting of the amino acid sequence of SEQ ID NO: 37 and having a disulfide bond formed by the cysteine residues at positions 249 and 254;
(E-a-9) a peptide consisting of the amino acid sequence of SEQ ID NO: 41, or a peptide consisting of the amino acid sequence of SEQ ID NO: 41 and having a disulfide bond formed by the cysteine residues at positions 251 and 256;
(E-a-10) a peptide consisting of the amino acid sequence of SEQ ID NO: 43, or a peptide consisting of the amino acid sequence of SEQ ID NO: 43 and having a disulfide bond formed by the cysteine residues at positions 251 and 256;
(E-a-11) a peptide consisting of the amino acid sequence of SEQ ID NO: 45, or a peptide consisting of the amino acid sequence of SEQ ID NO: 45 and having a disulfide bond formed by the cysteine residues at positions 246 and 251;
(E-a-12) a peptide consisting of the amino acid sequence of SEQ ID NO: 47, or a peptide consisting of the amino acid sequence of SEQ ID NO: 47 and having a disulfide bond formed by the cysteine residues at positions 246 and 251;
(E-g) any peptide of (E-a-1) to (E-a-12) wherein the disulfide bond of the peptide is substituted with an ethylene group and the peptide has adrenomedullin activity;
(E-h) any peptide of (E-a-1) to (E-g) wherein the peptide has the amino acid sequence comprising deletion, substitution, or addition of one to fifteen amino acid residues and has adrenomedullin activity;
(E-i) any peptide of (E-a-1) to (E-h) wherein the peptide is amidated at the C-terminus thereof; and
(E-j) any peptide of (E-a-1) to (E-h) wherein the peptide has a glycine residue added to the C-terminus thereof.

(9) The compound according to the embodiment (8), wherein the compound represented by formula (I) is a peptide selected from the group consisting of:
(E-a-1) a peptide consisting of the amino acid sequence of SEQ ID NO: 15, or a peptide consisting of the amino acid sequence of SEQ ID NO: 15 and having a disulfide bond formed by the cysteine residues at positions 259 and 264;
(E-a-2) a peptide consisting of the amino acid sequence of SEQ ID NO: 17, or a peptide consisting of the amino acid sequence of SEQ ID NO: 17 and having a disulfide bond formed by the cysteine residues at positions 259 and 264;
(E-a-3) a peptide consisting of the amino acid sequence of SEQ ID NO: 19, or a peptide consisting of the amino acid sequence of SEQ ID NO: 19 and having a disulfide bond formed by the cysteine residues at positions 256 and 261;
(E-a-4) a peptide consisting of the amino acid sequence of SEQ ID NO: 21, or a peptide consisting of the amino acid sequence of SEQ ID NO: 21 and having a disulfide bond formed by the cysteine residues at positions 256 and 261;
(E-a-5) a peptide consisting of the amino acid sequence of SEQ ID NO: 31, or a peptide consisting of the amino acid sequence of SEQ ID NO: 31 and having a disulfide bond formed by the cysteine residues at positions 254 and 259;
(E-a-6) a peptide consisting of the amino acid sequence of SEQ ID NO: 33, or a peptide consisting of the amino acid sequence of SEQ ID NO: 33 and having a disulfide bond formed by the cysteine residues at positions 254 and 259;
(E-a-7) a peptide consisting of the amino acid sequence of SEQ ID NO: 35, or a peptide consisting of the amino acid sequence of SEQ ID NO: 35 and having a disulfide bond formed by the cysteine residues at positions 249 and 254;
(E-a-8) a peptide consisting of the amino acid sequence of SEQ ID NO: 37, or a peptide consisting of the amino acid sequence of SEQ ID NO: 37 and having a disulfide bond formed by the cysteine residues at positions 249 and 254;
(E-a-9) a peptide consisting of the amino acid sequence of SEQ ID NO: 41, or a peptide consisting of the amino acid sequence of SEQ ID NO: 41 and having a disulfide bond formed by the cysteine residues at positions 251 and 256;
(E-a-10) a peptide consisting of the amino acid sequence of SEQ ID NO: 43, or a peptide consisting of the amino acid sequence of SEQ ID NO: 43 and having a disulfide bond formed by the cysteine residues at positions 251 and 256;
(E-a-11) a peptide consisting of the amino acid sequence of SEQ ID NO: 45, or a peptide consisting of the amino acid sequence of SEQ ID NO: 45 and having a disulfide bond formed by the cysteine residues at positions 246 and 251;
(E-a-12) a peptide consisting of the amino acid sequence of SEQ ID NO: 47, or a peptide consisting of the amino acid sequence of SEQ ID NO: 47 and having a disulfide bond formed by the cysteine residues at positions 246 and 251; and
(E-i) any peptide of (E-a-1) to (E-a-12) wherein the peptide is amidated at the C-terminus thereof.

(10) An isolated nucleic acid comprising a nucleotide sequence encoding the compound according to any of the embodiments (1) to (9).

(11) A method for producing the compound according to any of the embodiments (1) to (9) or a salt thereof, or a hydrate thereof, comprising an expression step of overexpressing the compound according to any of the embodiments (1) to (9) in a host cell capable of producing the compound.

(12) A medicament comprising the compound according to any of the embodiments (1) to (9) or a pharmaceutically acceptable salt thereof, or a pharmaceutically acceptable hydrate thereof as an active ingredient.

(13) The medicament according to the embodiment (12) for use in the prevention or treatment of a cardiovascular disease, an inflammatory disease, a vascular disease, or a renal disease.

(14) An agent for preventing or treating a cardiovascular disease, an inflammatory disease, a vascular disease, or a renal disease, wherein the agent comprises the compound according to any of the embodiments (1) to (9) or a pharmaceutically acceptable salt thereof, or a pharmaceutically acceptable hydrate thereof as an active ingredient.

(15) A pharmaceutical composition comprising the compound according to any of the embodiments (1) to (9) or a pharmaceutically acceptable salt thereof, or a pharmaceutically acceptable hydrate thereof and one or more pharmaceutically acceptable carriers.

(16) The pharmaceutical composition according to the embodiment (15) for use in the prevention or treatment of a cardiovascular disease, an inflammatory disease, a vascular disease, or a renal disease.

(17) A method for preventing or treating a condition, disease, and/or disorder, comprising administering to a subject in need of prevention or treatment of the condition, disease, and/or disorder an effective amount of the compound according to any of the embodiments (1) to (9) or a pharmaceutically acceptable salt thereof, or a pharmaceutically acceptable hydrate thereof.

(18) The method according to the embodiment (17) wherein the condition, disease, and/or disorder is a cardiovascular disease, an inflammatory disease, a vascular disease, or a renal disease.

(19) The compound according to any of the embodiments (1) to (9) or a pharmaceutically acceptable salt thereof, or a pharmaceutically acceptable hydrate thereof for use in the prevention or treatment of a condition, disease, and/or disorder.

(20) The compound according to the embodiment (19) wherein the condition, disease, and/or disorder is a cardiovascular disease, an inflammatory disease, a vascular disease, or a renal disease.

(21) Use of the compound according to any of the embodiments (1) to (9) or a pharmaceutically acceptable salt thereof, or a pharmaceutically acceptable hydrate thereof in the manufacture of a medicament for the prevention or treatment of a condition, disease, and/or disorder.

(22) The use according to the embodiment (21) wherein the condition, disease, and/or disorder is a cardiovascular disease, an inflammatory disease, a vascular disease, or a renal disease.

Advantageous Effects of Invention

The invention can provide novel adrenomedullin derivatives sustainable for a long period which are capable of substantially suppressing unwanted side effects while maintaining pharmacological effects of adrenomedullin.

The present specification includes contents described in the specification and/or drawings of Japanese patent application No. 2017-064369 to which the present application claims priority.

DESCRIPTION OF EMBODIMENTS

Figure 1:
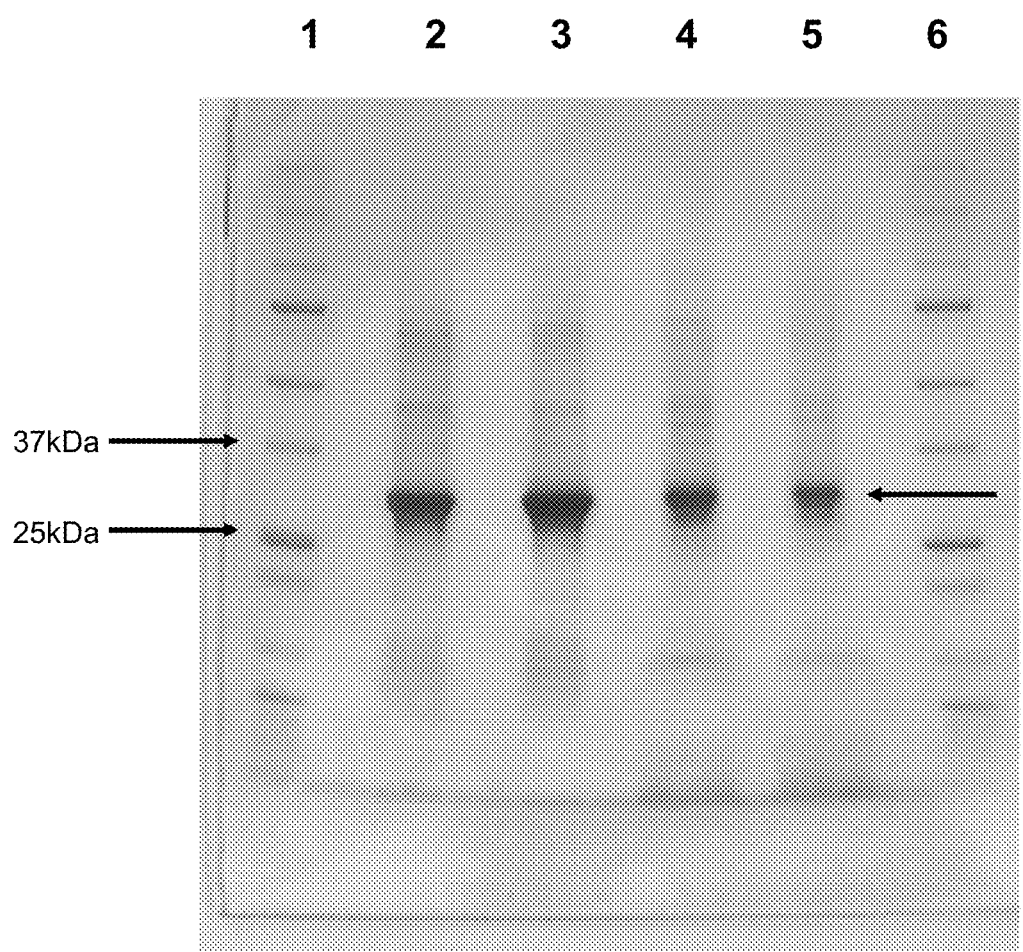
FIG. 1 shows results of separating adrenomedullin derivatives of Examples 1, 2, 3 and 4 by SDS-PAGE. In the figure, lanes 1 and 6 depict a molecular weight standard, and lanes 2, 3, 4 and 5 depict precipitated fractions obtained from recombinants of the adrenomedullin derivatives of Examples 1, 2, 3 and 4.

<1. Adrenomedullin Derivative>
An aspect of the invention relates to a compound represented by formula (I):

$$A\text{-}L\text{-}B \quad (I)$$

or a salt thereof, or a hydrate thereof. In the present specification, the compound represented by formula (I) may be described as "adrenomedullin derivative".

In the invention, adrenomedullin (AM) may not only be a peptide derived from human and isolated and identified from human pheochromocytoma (SEQ ID NO: 1, Non Patent Literature 1), but also be a peptide derived from other non-human mammals (such as warm-blooded animals), which is an ortholog, including, for example, pig (SEQ ID NO: 4), dog (SEQ ID NO: 6), cattle (SEQ ID NO: 8), rat (SEQ ID NO: 10), or mouse (SEQ ID NO: 12). In a living body, each of these peptides has a disulfide bond formed by two cysteine residues in the amino acid sequence and is amidated at the C-terminus thereof. In the present specification, the peptide having a disulfide bond and C-terminal amide group may be described as "natural adrenomedullin" or simply "adrenomedullin". The invention can be applied to any of the peptides described above.

In the present specification, "C-terminal amidation" means an aspect of post-translational modification of a peptide in a living body, and specifically means a reaction in which the main chain carboxyl group of C-terminal amino acid residue of the peptide is converted into an amide group.

In the present specification, "formation of a disulfide bond between cysteine residues" or "disulfide bond formation by cysteine residues" means an aspect of post-translational modification of the peptide in a living body, and specifically means a reaction in which two cysteine residues in the amino acid sequence of the peptide form a disulfide bond (—S—S—). Many bioactive peptides produced in a living body are initially biosynthesized as a precursor protein with larger molecular weight. The precursor protein is subject to post-translational modifications, such as C-terminal amidation and/or disulfide bond formation by cysteine residues, during the process of intracellular transport to give a mature bioactive peptide. The C-terminal amidation typically proceeds by a C-terminal amidating enzyme that acts on the precursor protein. For a bioactive peptide having a C-terminal amide group, the precursor protein has a Gly residue bound to the C-terminal carboxyl group to be amidated and the Gly residue is converted into the C-terminal amide group by the C-terminal amidating enzyme. The C-terminal propeptide in the precursor protein has a repeat sequence comprising a combination of basic amino acid residues, such as Lys-Arg or Arg-Arg (Mizuno, Journal of Japanese Biochemical Society, 61(12): 1435-1461 (1989)). Disulfide bond formation by cysteine residues can proceed under oxidative conditions. Disulfide bond formation by cysteine residues in a living body typically proceeds by a protein disulfide isomerase that acts on the precursor protein.

Adrenomedullin, a known bioactive substance, is a peptide. This may cause a medicament comprising adrenomedullin as an active ingredient to act effectively in living bodies in subjects (such as human patients) only for a very short time. Accordingly, attempts have been made to prolong half-life in a living body and improve pharmacokinetics by means of forms of adrenomedullin derivatives in which other groups such as polyethylene glycol (PEG) are linked to adrenomedullin (Patent Literatures 4 to 6 and Non Patent Literature 10). However, in the case of linking a relatively large group such as a PEG group to a relatively small peptide such as adrenomedullin, various properties of the resulting adrenomedullin derivative may vary largely depending on the molecular weight of the PEG group. In the case of linking other groups to the side chain of an amino acid residue of adrenomedullin, the conformation of the adrenomedullin moiety may be changed to reduce the affinity for an AM receptor recognizing adrenomedullin. In such a case, pharmacological effects as adrenomedullin of the resulting adrenomedullin derivative may be reduced.

Adrenomedullin has a strong vasodilatory effect. This strong vasodilatory effect may cause unwanted side effects (such as excessive decreased blood pressure, tachycardia associated with increased reflex sympathetic nerve activity, and/or increased activity of renin) when a therapeutically effective amount of adrenomedullin or a derivative thereof is administered in a single dose. The occurrence of such side effects may become a problem when adrenomedullin or a derivative thereof is used, particularly, in the expectation that pharmacological effects other than a vasodilatory effect are exerted. To avoid generating the problems described above, a medicament comprising adrenomedullin or a derivative thereof as an active ingredient is required to be administered to subjects via continuous intravenous infusion. Such a mode of administration may force subjects to bear an undue burden.

Adrenomedullin derivatives which maintain pharmacological effects of adrenomedullin and have improved sustainability in a living body are expected to be capable of exerting pharmacological effects of adrenomedullin without substantially causing unwanted side effects, even when administered to subjects in a single dose.

The present inventors have found that linking of the N-terminal α-amino group of adrenomedullin to an Fc region of an immunoglobulin via a linking group of a peptide having a specific amino acid sequence can retain bioactivity of adrenomedullin. It is known in the art that a fusion protein comprising an Fc region of an immunoglobulin linked to a specific protein or peptide is capable of prolonging half-life in the bodies of subjects when administered to the subjects, as compared to the parent compound protein or peptide (e.g., Patent Literatures 8 and 9). Thus, the compound represented by formula (I) according to the aspect can be applied to a condition, disease, and/or disorder that can be prevented or treated with adrenomedullin to sustainably prevent or treat the condition, disease, and/or disorder while substantially suppressing unwanted side effects.

In formula (I), B is required to be a peptide moiety derived from adrenomedullin or a modified form thereof with adrenomedullin activity. In the invention, "peptide moiety derived from adrenomedullin or a modified form thereof with adrenomedullin activity" means a monovalent radical with a structure derived from adrenomedullin or the modified form thereof with adrenomedullin activity by removal of one hydrogen atom (commonly, one hydrogen atom of an amino group, typically one hydrogen atom of the N-terminal α-amino group). In the invention, "a modified form of adrenomedullin" means a peptide chemically modified from natural adrenomedullin as described above. In the invention, "adrenomedullin activity" means bioactivity that adrenomedullin has. The adrenomedullin activity can include the following:

(1) Cardiovascular: a vasodilatory effect, an effect of lowering blood pressure, an effect of suppressing increase in blood pressure, an effect of increasing cardiac output or improving cardiac insufficiency, an effect of improving pulmonary hypertension, an angiogenic effect, a lymphangiogenic effect, an effect of improving vascular endothelial function, an antiarteriosclerotic effect, a myocardial protective effect (such as a myocardial protective effect in ischemic reperfusion disorder or inflammation), an effect of preventing postmyocardial remodeling, an effect of suppressing cardiac hypertrophy, and an effect of suppressing an angiotensin-converting enzyme.

(2) Kidney and water and electrolyte system: a diuretic effect, a natriuretic effect, an effect of suppressing antidiuretic hormone, an aldosterone-reducing effect, a renoprotective effect (such as a renoprotective effect in high blood pressure or ischemic reperfusion disorder), an effect of suppressing drinking behavior, and an effect of suppressing salt requirement.

(3) Brain and nervous system: an effect of neuroprotection and preventing encephalopathy, an anti-inflammatory effect, an effect of suppressing apoptosis (such as an effect of suppressing apoptosis in ischemic reperfusion disorder or inflammation), an effect of maintaining autoregulatory capacity, an effect of suppressing oxidative stress, an effect of improving dementia, and a sympathoinhibitory effect.

(4) Urogenital: an effect of improving erection, an effect of improving blood flow, and an implantation-promoting effect.

(5) Gastrointestinal system: an antiulcer effect, a tissue repair effect, an effect of neogenesis of mucous membrane, an effect of improving blood flow, an anti-inflammatory effect, and an effect of improving liver function.

(6) Orthopedics: an effect of stimulating osteoblast and an effect of improving arthritis.

(7) Endocrine metabolic system: an adipocyte-differentiating effect, an effect of regulating lipolysis, an effect of improving insulin sensitivity, an effect of controlling insulin secretion, an effect of suppressing antidiuretic hormone secretion, and an effect of suppressing aldosterone secretion.

(8) Other: an effect of improving circulation, an anti-inflammatory effect, an effect of modulating cytokine, an organ protective effect, an effect of suppressing oxidative stress, an effect of repairing tissue (such as an anti-decubitus effect), an effect of improving septic shock, an effect of suppressing multiple organ failure, an effect of suppressing auto-immune disease, an antimicrobial effect, a hair growth effect, and a pilatory effect.

The blood pressure-lowering effect is preferably a vasodilatory hypotensive effect. The anti-inflammatory effect in the gastrointestinal system is preferably an effect of preventing or treating inflammatory bowel diseases including a steroid-resistant or steroid-dependent inflammatory bowel disease (such as ulcerative colitis, Crohn's disease, or intestinal tract Behcet's disease). The adrenomedullin activity will be exerted via increased concentration of intracellular cAMP. Thus, the increased concentration of intracellular cAMP can be considered as an index of adrenomedullin activity. The peptide moiety B derived from adrenomedullin or a modified form thereof having the bioactivity as described above enables the compound represented by formula (I) according to the aspect to exert bioactivity substantially approximately equivalent to that of natural adrenomedullin (i.e., adrenomedullin activity).

The adrenomedullin or a modified form thereof with adrenomedullin activity is preferably a peptide selected from the group consisting of:

(i) a peptide consisting of an amino acid sequence of adrenomedullin,
(ii) a peptide that consists of an amino acid sequence of adrenomedullin and has a disulfide bond formed by two cysteine residues in the amino acid sequence,
(iii) the peptide of (ii) wherein the disulfide bond of the peptide is substituted with an ethylene group and the peptide has adrenomedullin activity,
(iv) any peptide of (i) to (iii) wherein the peptide has the amino acid sequence comprising deletion, substitution, or addition of one to fifteen amino acid residues and has adrenomedullin activity,
(v) any peptide of (i) to (iv) wherein the peptide is amidated at the C-terminus thereof, and
(vi) any peptide of (i) to (iv) wherein the peptide has a glycine residue added to the C-terminus thereof.

In one embodiment, the adrenomedullin or a modified form thereof with adrenomedullin activity is more preferably a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(v) the peptide of (i) or (ii) wherein the peptide is amidated at the C-terminus thereof, and
(vi) the peptide of (i) or (ii) wherein the peptide has a glycine residue added to the C-terminus thereof.

In the peptides of (i) to (vi), a peptide involved in (v), which consists of the amino acid sequence of adrenomedullin, is amidated at the C-terminus thereof, and has a disulfide bond formed by two cysteine residues in the amino acid sequence, represents a mature natural adrenomedullin. A peptide of (i) consisting of an amino acid sequence of adrenomedullin represents a form of natural adrenomedullin prior to post-translational modification including C-terminal amidation and disulfide bond formation by cysteine residues (i.e., an immature form). Other peptides except peptides described above in the peptides of (i) to (vi) represent modified forms of adrenomedullin.

The peptide of (ii) can be formed by oxidizing thiol groups of two cysteine residues in the peptide of (i) with air or with a suitable oxidizing agent to form a disulfide bond. The peptide of (ii) can be used to establish the conformation of the peptide moiety B similar to that of natural adrenomedullin. This similar conformation can lead adrenomedullin activity of a compound represented by formula (I) to an activity substantially approximately equivalent to that of natural adrenomedullin.

The peptide of (iii) can be formed by converting the disulfide bond in the peptide of (ii) into an ethylene group. The substitution of the disulfide bond to an ethylene group can be accomplished by any method well known in the art (O. Keller et al., Helv. Chim. Acta, 1974, Volume 57, p. 1253). The peptide of (iii) can be used to stabilize the conformation of peptide moiety B. The stabilized conformation allows a compound represented by formula (I) to sustainably exert adrenomedullin activity in a living body.

In the peptide of (iv), the number of amino acid residues deleted, substituted, or added preferably ranges from 1 to 15, more preferably from 1 to 10, further preferably from 1 to 8, especially preferably from 1 to 5, and most preferably from 1 to 3. A suitable peptide of (iv) is any peptide of (i) to (iii) wherein the peptide has deletion of amino acid residues at positions 1 to 15, positions 1 to 12, positions 1 to 10, positions 1 to 8, positions 1 to 5, or positions 1 to 3 from the N-terminus thereof and has adrenomedullin activity. A more suitable peptide of (iv) is any peptide of (i) to (iii) wherein the peptide has deletion of amino acid residues at positions 1 to 15, positions 1 to 10, or positions 1 to 5 from the N-terminus thereof and has adrenomedullin activity. The suitable peptide may have further deletion, substitution, or addition of one or more (such as 1 to 5, 1 to 3, or 1 or 2) amino acid residues. The peptide of
(iv) can be used to achieve adrenomedullin activity of a compound represented by formula (I) substantially approximately equivalent to that of natural adrenomedullin. Also, the peptide of
(iv) can be used to sustainably exert adrenomedullin activity of a compound represented by formula (I) in a living body.

The peptide of (vi) can be converted to the peptide of (v) by a C-terminal amidating enzyme which can convert a glycine residue at the C-terminus of the peptide of (vi) into an amide group. Therefore, the peptide of (vi) can be administered to a subject to form the peptide amidated at the C-terminus thereof in the living body of the subject after a certain period of time. Thus, a compound represented by formula (I) can sustainably exert adrenomedullin activity in a living body.

The adrenomedullin or a modified form thereof is more preferably a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of the SEQ ID NO: 4, or a peptide consisting of the amino acid sequence of the SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(g) any peptide of (a) to (f) wherein the disulfide bond of the peptide is substituted with an ethylene group and the peptide has adrenomedullin activity;
(h) any peptide of (a) to (g) wherein the peptide has the amino acid sequence comprising deletion, substitution, or addition of one to fifteen amino acid residues and has adrenomedullin activity;
(i) any peptide of (a) to (h) wherein the peptide is amidated at the C-terminus thereof; and
(j) any peptide of (a) to (h) wherein the peptide has a glycine residue added to the C-terminus thereof.

In one embodiment, the adrenomedullin or a modified form thereof is further preferably a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;

(b) a peptide consisting of the amino acid sequence of SEQ ID NO: 4, or a peptide consisting of the amino acid sequence of SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(i) any peptide of (a) to (f) wherein the peptide is amidated at the C-terminus thereof; and
(j) any peptide of (a) to (f) wherein the peptide has a glycine residue added to the C-terminus thereof.

In the peptide of (h), the number of amino acid residues deleted, substituted, or added preferably ranges from 1 to 12, more preferably from 1 to 10, further preferably from 1 to 8, especially preferably from 1 to 5, and most preferably from 1 to 3. A suitable peptide of (h) is any peptide of (a) to (g) wherein the peptide has deletion of amino acid residues at positions 1 to 15, positions 1 to 12, positions 1 to 10, positions 1 to 8, positions 1 to 5, or positions 1 to 3 from the N-terminus thereof and has adrenomedullin activity. A more suitable peptide of (h) is any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity. The suitable peptide may have further deletion, substitution, or addition of one or more (such as 1 to 5, 1 to 3, or 1 or 2) amino acids. The peptide of (h) can be used to achieve adrenomedullin activity of a compound represented by formula (I) substantially approximately equivalent to that of natural adrenomedullin. Also, the peptide of (h) can be used to sustainably exert adrenomedullin activity of a compound represented by formula (I) in a living body.

In formula (I), A is an Fc region of an immunoglobulin. A is preferably an Fc region of immunoglobulin G1 (IgG1) or an Fc region of immunoglobulin G4 (IgG4). It is known in the art that a fusion protein comprising an Fc region of an immunoglobulin linked to a specific protein or peptide is capable of prolonging half-life in the bodies of subjects when administered to the subjects, as compared to a protein or peptide being its parent compound (e.g., Patent Literatures 8 and 9). Therefore, the compound represented by formula (I) according to the aspect having the Fc region A of an immunoglobulin can sustainably exert adrenomedullin activity in a living body.

In formula (I), the mammal that serves as the origin of the Fc region A of an immunoglobulin can be suitably selected on the basis of a subject to which a medicament comprising the compound represented by formula (I) as an active ingredient according to an aspect of the invention is applied, which will be described below. A is preferably an Fc region of an immunoglobulin derived from human or non-human mammal (such as warm-blooded animal including pig, dog, cattle, rat, mouse, guinea pig, rabbit, chicken, sheep, cat, monkey, hamadryas baboon, or chimpanzee) and more preferably an Fc region of an immunoglobulin derived from the same human or non-human mammal as the subject to which the medicament according to an aspect of the invention is applied. The compound represented by formula (I) according to the aspect having the Fc region of an immunoglobulin derived from human or non-human mammal described above can sustainably exert adrenomedullin activity in a living body while maintaining pharmacological effects of natural adrenomedullin.

In formula (I), L is a linking group comprising a peptide having any given amino acid sequence. L is not limited and a linking group comprising a peptide having an amino acid sequence of (GGGS)n (SEQ ID NO: 26) (n is an integer ranging from 2 to 10 and preferably an integer ranging from 4 to 6), (GGGGS)n (SEQ ID NO: 27) (n is an integer ranging from 2 to 6 and preferably 3), (GGGS)n+GGGK (SEQ ID NOs: 26 and 28) (n is an integer ranging from 1 to 9 and preferably an integer ranging from 3 to 5), or (GGGGS)n+GGGGK (SEQ ID NOs: 27 and 29) (n is an integer ranging from 1 to 5 and preferably 2) can be used when n is defined as the number of repeats. In the amino acid sequence described above, the number of G and the number n of repeats in the repeat unit may be suitably changed. L is particularly preferably a linking group comprising a peptide having the following amino acid sequence:

```
                                     (SEQ ID NO: 22)
GGGGSGGGGSGGGGS;
or
                                     (SEQ ID NO: 24)
GGGGSGGGGSGGGGK.
```

The compound represented by formula (I) according to the aspect comprising the Fc region A of an immunoglobulin linked to the peptide moiety B derived from adrenomedullin or a modified form thereof with adrenomedullin activity via the linking group L having the amino acid sequence described above can sustainably exert adrenomedullin activity in a living body while maintaining pharmacological effects of natural adrenomedullin.

In formula (I), preferably, the Fc region A is linked to the other moieties through a peptide bond formed by the C-terminal carboxyl group of the Fc region A and the N-terminal α-amino group of the linking group L, and the peptide moiety B is linked to the other moieties through a peptide bond formed by the N-terminal α-amino group of the peptide moiety B and the C-terminal carboxyl group of the linking group L. That is, the compound represented by formula (I) according to the aspect has a protein or polypeptide structure as a whole. The compound represented by formula (I) according to the aspect having such a structure can have high biocompatibility. Therefore, the compound represented by formula (I) according to the aspect can sustainably exert adrenomedullin activity in a living body while suppressing unwanted side effects.

In a suitable compound represented by formula (I),
A is an Fc region of immunoglobulin G1 (IgG1) or an Fc region of immunoglobulin G4 (IgG4),
B is a peptide moiety derived from adrenomedullin or a modified form thereof with adrenomedullin activity, the adrenomedullin or the modified form thereof being a peptide selected from the group consisting of:

(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 4, or a peptide consisting of the amino acid sequence of SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(i) any peptide of (a) to (f) wherein the peptide is amidated at the C-terminus thereof; and
(j) any peptide of (a) to (f) wherein the peptide has a glycine residue added to the C-terminus thereof, and L is a linking group comprising a peptide having the following amino acid sequence:

GGGGSGGGGSGGGGS;   (SEQ ID NO: 22)

or

GGGGSGGGGSGGGGK,   (SEQ ID NO: 24)

and

Fc region A is linked to the other moieties through a peptide bond formed by the C-terminal carboxyl group of the Fc region A and the N-terminal α-amino group of the linking group L, and the peptide moiety B is linked to the other moieties through a peptide bond formed by the N-terminal α-amino group of the peptide moiety B and the C-terminal carboxyl group of the linking group L.

In a particularly suitable compound represented by formula (I), the adrenomedullin or the modified form thereof is a peptide selected from the group consisting of:
(E-a-1) a peptide consisting of the amino acid sequence of SEQ ID NO: 15, or a peptide consisting of the amino acid sequence of SEQ ID NO: 15 and having a disulfide bond formed by the cysteine residues at positions 259 and 264;
(E-a-2) a peptide consisting of the amino acid sequence of SEQ ID NO: 17, or a peptide consisting of the amino acid sequence of SEQ ID NO: 17 and having a disulfide bond formed by the cysteine residues at positions 259 and 264;
(E-a-3) a peptide consisting of the amino acid sequence of SEQ ID NO: 19, or a peptide consisting of the amino acid sequence of SEQ ID NO: 19 and having a disulfide bond formed by the cysteine residues at positions 256 and 261;
(E-a-4) a peptide consisting of the amino acid sequence of SEQ ID NO: 21, or a peptide consisting of the amino acid sequence of SEQ ID NO: 21 and having a disulfide bond formed by the cysteine residues at positions 256 and 261;
(E-a-5) a peptide consisting of the amino acid sequence of SEQ ID NO: 31, or a peptide consisting of the amino acid sequence of SEQ ID NO: 31 and having a disulfide bond formed by the cysteine residues at positions 254 and 259;
(E-a-6) a peptide consisting of the amino acid sequence of SEQ ID NO: 33, or a peptide consisting of the amino acid sequence of SEQ ID NO: 33 and having a disulfide bond formed by the cysteine residues at positions 254 and 259;
(E-a-7) a peptide consisting of the amino acid sequence of SEQ ID NO: 35, or a peptide consisting of the amino acid sequence of SEQ ID NO: 35 and having a disulfide bond formed by the cysteine residues at positions 249 and 254;
(E-a-8) a peptide consisting of the amino acid sequence of SEQ ID NO: 37, or a peptide consisting of the amino acid sequence of SEQ ID NO: 37 and having a disulfide bond formed by the cysteine residues at positions 249 and 254;
(E-a-9) a peptide consisting of the amino acid sequence of SEQ ID NO: 41, or a peptide consisting of the amino acid sequence of SEQ ID NO: 41 and having a disulfide bond formed by the cysteine residues at positions 251 and 256;
(E-a-10) a peptide consisting of the amino acid sequence of SEQ ID NO: 43, or a peptide consisting of the amino acid sequence of SEQ ID NO: 43 and having a disulfide bond formed by the cysteine residues at positions 251 and 256;
(E-a-11) a peptide consisting of the amino acid sequence of SEQ ID NO: 45, or a peptide consisting of the amino acid sequence of SEQ ID NO: 45 and having a disulfide bond formed by the cysteine residues at positions 246 and 251;
(E-a-12) a peptide consisting of the amino acid sequence of SEQ ID NO: 47, or a peptide consisting of the amino acid sequence of SEQ ID NO: 47 and having a disulfide bond formed by the cysteine residues at positions 246 and 251;
(E-g) any peptide of (E-a-1) to (E-a-12) wherein the disulfide bond of the peptide is substituted with an ethylene group and the peptide has adrenomedullin activity;
(E-h) any peptide of (E-a-1) to (E-g) wherein the peptide has the amino acid sequence comprising deletion, substitution, or addition of one to fifteen amino acid residues and has adrenomedullin activity;
(E-i) any peptide of (E-a-1) to (E-h) wherein the peptide is amidated at the C-terminus thereof and
(E-j) any peptide of (E-a) to (E-h) wherein the peptide has a glycine residue added to the C-terminus thereof.

A compound represented by formula (I) according to the aspect having the properties described above can substantially suppress unwanted side effects and sustainably exert adrenomedullin activity in a living body, while maintaining pharmacological effects of natural adrenomedullin.

In the invention, a compound represented by formula (I) includes not only the compound itself but also a salt thereof. When a compound represented by formula (I) is in the form of salt, it is preferably a pharmaceutically acceptable salt. Counterions in a salt of the compound represented by formula (I) preferably include, but are not limited to, for example, cations such as a sodium, potassium, calcium, magnesium, or substituted or unsubstituted ammonium ion, or anions such as a chloride, bromide, iodide, phosphate, nitrate, sulfate, carbonate, bicarbonate, perchlorate, formate, acetate, trifluoroacetate, propionate, lactate, maleate, hydroxymaleate, methylmaleate, fumarate, adipate, benzoate, 2-acetoxybenzoate, p-aminobenzoate, nicotinate, cinnamate, ascorbate, pamoate, succinate, salicylate, bismethylenesalicylate, oxalate, tartrate, malate, citrate, gluconate, aspartate, stearate, palmitate, itaconate, glycolate, glutamate, benzenesulfonate, cyclohexylsulfamate, methanesulfonate, ethanesulfonate, isethionate, benzenesulfonate, p-toluenesulfonate, or naphthalenesulfonate ion. When a compound represented by formula (I) is in the form of salt with any of the counterions, adrenomedullin activity of the compounds can be substantially approximately equivalent to that of natural adrenomedullin.

In the invention, a compound represented by formula (I) includes not only the compound itself but also a solvate of the compound or a salt thereof. When a compound represented by formula (I) or a salt thereof is in the form of a solvate, it is preferably a pharmaceutically acceptable solvate. Solvents that can form solvates with the compound or a salt thereof include, but are not limited to, for example, water or organic solvents such as methanol, ethanol, 2-propanol (isopropyl alcohol), dimethyl sulfoxide (DMSO), acetic acid, ethanolamine, acetonitrile, or ethyl acetate. When a compound represented by formula (I) or a salt thereof is in the form of solvate with any of the solvents described above, adrenomedullin activity of the compounds can be substantially approximately equivalent to that of natural adrenomedullin.

In the invention, a compound represented by formula (I) includes not only the compound itself described above or below but also a protected form thereof. In the present specification, a "protected form" means a form in which any suitable protecting group is introduced into one or more functional groups (such as a side-chain amino group of lysine residue) of the compound. In the present specification, a "protecting group" means a group that is introduced into a specific functional group to prevent any unwanted reaction from proceeding, will be removed quantitatively under a specific reaction condition, and is substantially stable, or inactive, under any reaction condition other than the specific reaction condition. Protecting groups that can form protected forms of the compounds include, but are not limited to, for example, t-butoxycarbonyl (Boc), 2-bromobenzyloxycarbonyl (BrZ), 9-fluorenylmethoxycarbonyl (Fmoc), p-toluenesulfonyl (Tos), benzyl (Bzl), 4-methylbenzyl (4-MeBzl), 2-chlorobenzyloxycarbonyl (ClZ), cyclohexyl (cHex), and phenacyl (Pac); other protecting groups of amino groups include benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenyl)isopropyloxycarbonyl, 2-(3,5-dimethoxyphenyl)isopropyloxycarbonyl, p-phenylazobenzyloxycarbonyl, triphenylphosphonoethyloxycarbonyl, 9-fluorenylmethyloxycarbonyl, t-amyloxyoxycarbonyl, diisopropylmethyloxycarbonyl, isopropyloxycarbonyl, ethyloxycarbonyl, allyloxycarbonyl, 2-methylsulfonylethyloxycarbonyl, 2,2,2-trichloroethyloxycarbonyl, cyclopentyloxycarbonyl, cyclohexyloxycarbonyl, adamantyloxycarbonyl, isobornyloxycarbonyl, benzenesulfonyl, mesitylenesulfonyl, methoxytrimethylphenylsulfonyl, 2-nitrobenzensulfonyl, 2-nitrobenzenesulfenyl, 4-nitrobenzenesulfonyl, and 4-nitrobenzenesulfenyl; other protecting groups of carboxyl groups include methyl esters, ethyl esters, t-butyl esters, p-methoxybenzyl esters, and p-nitrobenzyl esters; other side-chain protecting groups of Arg include 2,2,4,6,7-pentamethyl-2,3-dihydrobenzofuran-5-sulfonyl, 4-methoxy-2,3,6-trimethylbenzenesulphonyl, 2,2,5,7,8-pentamethylchroman-6-sulfonyl, and 2-methoxybenzenesulfonyl; other protecting groups of Tyr include 2,6-dichlorobenzyl, t-butyl, and cyclohexyl; other protecting groups of Cys include 4-methoxybenzyl, t-butyl, trityl, acetamidomethyl, and 3-nitro-2-pyridine sulfenyl; other protecting groups of His include benzyloxymethyl, p-methoxybenzyloxymethyl, t-butoxymethyl, trityl, and 2,4-dinitrophenyl; and other protecting groups of Ser and Thr include t-butyl. When a compound represented by formula (I) is in a protected form with any of the protecting groups described above, adrenomedullin activity of the compound can be substantially approximately equivalent to that of natural adrenomedullin.

In the invention, a compound represented by formula (I) includes individual enantiomer and diastereomer of the compounds, and mixtures of stereoisomeric forms of the compounds such as racemates.

A compound represented by formula (I) according to the aspect having the properties described above can sustainably exert adrenomedullin activity in a living body, while maintaining pharmacological effects of natural adrenomedullin.

<2. Pharmaceutical Use of Adrenomedullin Derivatives>

A compound represented by formula (I) according to an aspect of the invention can sustainably exert bioactivity substantially approximately equivalent to that of adrenomedullin, which is the parent molecule of the compound, (i.e., adrenomedullin activity) in a living body. Therefore, another aspect of the invention relates to a medicament comprising a compound represented by formula (I) according to an aspect of the invention as an active ingredient.

A compound represented by formula (I) according to an aspect of the invention may be used alone or in combination with one or more pharmaceutically acceptable components when the compound is applied to pharmaceutical use. A medicament according to the aspect can be formulated into various dosage forms commonly used in the art depending on the desired mode of administration. Thus, the medicament according to the aspect can also be provided in the form of a pharmaceutical composition comprising a compound represented by formula (I) according to an aspect of the invention and one or more pharmaceutically acceptable carriers. Pharmaceutical compositions according to an aspect of the invention may comprise, in addition to the components described above, one or more pharmaceutically acceptable carriers, excipients, binders, vehicles, dissolution aids, preservatives, stabilizers, bulking agents, lubricants, surfactants, oily liquids, buffering agents, soothing agents, antioxidants, sweetening agents, flavoring agents, and so forth.

Dosage forms of medicaments comprising a compound represented by formula (I) according to an aspect of the invention as an active ingredient are not particularly limited and may be a formulation for parenteral or oral administration. Dosage forms of medicaments according to the aspect may also be a formulation in unit dosage form or in multiple dosage form. Formulations for use in parenteral administration include, for example, injections such as sterile solutions or suspensions in water or any other pharmaceutically acceptable liquid. Additive agents that can be admixed into the injections include, but are not limited to, for example, vehicles such as physiological saline and isotonic solutions comprising glucose or other pharmaceutic aids (such as D-sorbitol, D-mannitol, or sodium chloride); dissolution aids such as alcohols (such as ethanol or benzyl alcohol), esters (such as benzyl benzoate), and polyalcohols (such as propylene glycol or polyethylene glycol); nonionic surfactants such as polysorbate 80 or polyoxyethylene hydrogenated castor oil; oily liquids such as sesame oil or soybean oil; buffering agents such as phosphate buffer or sodium acetate buffer; soothing agents such as benzalkonium chloride or procaine hydrochloride; stabilizers such as human serum albumin or polyethylene glycol; preservatives; and antioxidants. The prepared injection will be generally filled in any suitable vial (such as an ampule) and preserved under an appropriate environment until use.

The formulations for use in oral administration include, for example, a tablet optionally coated with sugar coating or soluble film, a capsule, an elixir, a microcapsule, a syrup, and a suspension. Additive agents that can be admixed into tablets or capsules and so forth include, but are not limited to, for example, binders such as gelatin, cornstarch, gum tragacanth, and gum arabic; excipients such as crystalline cellulose; bulking agents such as cornstarch, gelatin, and alginate; lubricants such as magnesium stearate; sweetening agents such as sucrose, lactose, or saccharin; and flavoring agents such as peppermint, *Gaultheria adenothrix* oil, or cherry. A formulation may further include liquid carriers such as oils/fats when the formulation is in the form of a capsule.

The compound represented by formula (I) according to an aspect of the invention can sustainably exert adrenomedullin activity substantially approximately equivalent to that of adrenomedullin, which is the parent molecule of the compound, in a living body. Thus, a medicament comprising a compound represented by formula (I) according to an aspect of the invention as an active ingredient can be formulated into a depot formulation. In this case, the medicament according to the aspect in the dosage form of depot formulation can, for example, be implanted subcutaneously or intramuscularly or administered by intramuscular injection. The depot formulation of the medicament according to the aspect allows the compound represented by formula (I) according to an aspect of the invention to sustainably exert adrenomedullin activity for a long period of time.

The medicament comprising a compound represented by formula (I) according to an aspect of the invention as an active ingredient can be combined with one or more other drugs useful as medicaments. In this case, the medicament according to the aspect may be provided in the form of a single medicament comprising the compound represented by formula (I) according to an aspect of the invention and one or more other drugs, or may be provided in the form of a medicament combination or kit comprising a plurality of formulations into which the compound represented by formula (I) according to an aspect of the invention and one or more other drugs are separately formulated. For the medicament combination or kit, each formulation can be administered simultaneously or separately (such as sequentially).

For applying a compound represented by formula (I) according to an aspect of the invention to pharmaceutical use, the compound represented by formula (I) includes not only the compound itself but also a pharmaceutically acceptable salt thereof and a pharmaceutically acceptable solvate thereof. The pharmaceutically acceptable salts of a compound represented by formula (I) according to an aspect of the invention and pharmaceutically acceptable solvates thereof preferably include, but are not limited to, for example, salts or solvates exemplified above. When a compound represented by formula (I) is in the form of any of the salts or solvates described above, the compound can be applied to the desired pharmaceutical use.

A medicament comprising a compound represented by formula (I) according to an aspect of the invention as an active ingredient can prevent or treat various conditions, diseases, and/or disorders that will be prevented or treated with adrenomedullin. The conditions, diseases, and/or disorders include, but are not limited to, for example, the following:

(1) Cardiovascular diseases: cardiac insufficiency, pulmonary hypertension, arteriosclerosis obliterans, Buerger's disease, myocardial infarction, lymphedema, Kawasaki's disease, myocarditis, high blood pressure, organ dysfunctions due to high blood pressure, and arteriosclerosis.

(2) Kidney and water and electrolyte system disorders: kidney failure and nephritis.

(3) Brain and nervous system diseases: cerebral infarction, dementia, and encephalitis.

(4) Urogenital diseases: erectile dysfunction (ED).

(5) Gastrointestinal diseases: inflammatory bowel disease, ulcerative disease, intestinal Behcet's disease, and hepatic failure.

(6) Orthopedic disease: arthritis.

(7) Endocrine metabolic disease: diabetes and organ dysfunctions due to diabetes, and primary aldosteronism.

(8) Others: septic shock, auto-immune disease, multiple organ failure, pressure sore, wound healing, and alopecia.

The cardiovascular disease is preferably any of myocardial infarction, pulmonary hypertension, and cardiac insufficiency. The gastrointestinal disease is preferably any of inflammatory diseases including a steroid-resistant or steroid-dependent inflammatory bowel disease (such as ulcerative colitis, Crohn's disease, or intestinal tract Behcet's disease).

A compound represented by formula (I) according to an aspect of the invention has a structure in which adrenomedullin, which is a natural bioactive peptide, is linked to an Fc region of an immunoglobulin via a linking group of a peptide. This structure allows the compound represented by formula (I) according to an aspect of the invention to be safe and have low toxicity. Therefore, the medicament comprising the compound represented by formula (I) according to an aspect of the invention as an active ingredient can be applied to various subjects in need of prevention or treatment of the condition, disease, and/or disorder. The subjects are preferably human or non-human mammalian (such as warm-blooded animal including pig, dog, cattle, rat, mouse, guinea pig, rabbit, chicken, sheep, cat, monkey, hamadryas baboon, or chimpanzee) subjects or patients. The medicament according to the aspect can be administered to the subjects to prevent or treat various conditions, diseases, and/or disorders that will be prevented or treated with adrenomedullin.

In the present specification, "prevention" means that onset (development or occurrence) of a condition, disease, and/or disorder will be substantially precluded. On the other hand, in the present specification, "treatment" means suppression (such as suppression of progression), remission, restoration, and/or cure of a condition, disease, and/or disorder that has appeared (developed or occurred).

The compound represented by formula (I) according to an aspect of the invention can be used to prevent or treat the condition, disease, and/or disorder described above (such as a cardiovascular disease, inflammatory disease, vascular disease, or renal disease) in subjects with the condition, disease, and/or disorder. Therefore, the medicament according to the aspect is preferably a medicament for use in the prevention or treatment of the condition, disease, and/or disorder described above and is more preferably a medicament for use in the prevention or treatment of a cardiovascular disease, an inflammatory disease, a vascular disease, or a renal disease. The invention also relates to an agent for preventing or treating a cardiovascular disease, an inflammatory disease, a vascular disease, or a renal disease comprising a compound represented by formula (I) according to an aspect of the invention as an active ingredient. The compound represented by formula (I) according to an aspect of the invention can be used to prevent or treat the condition, disease, and/or disorder described above to sustainably prevent or treat the condition, disease, and/or disorder.

A compound represented by formula (I) according to an aspect of the invention can be used to prevent or treat the condition, disease, and/or disorder described above (such as a cardiovascular disease, inflammatory disease, vascular disease, or renal disease) in subjects with the condition, disease, and/or disorder. Therefore, another aspect of the invention is a method for preventing or treating the disease or condition described above, comprising administering an effective amount of a compound of the invention represented by formula (I) or a pharmaceutically acceptable salt thereof, or a pharmaceutically acceptable hydrate thereof to a subject in need of prevention or treatment of the condition, disease, and/or disorder described above. The condition, disease, and/or disorder are preferably any of cardiovascular diseases, inflammatory diseases, vascular diseases, and renal diseases. A compound represented by formula (I) according to an aspect of the invention can be administered to subjects in need of prevention or treatment of the condition, disease, and/or disorder to prevent or treat the condition, disease, and/or disorder.

Another aspect of the invention is a compound represented by formula (I) according to an aspect of the invention or a pharmaceutically acceptable salt thereof, or a pharmaceutically acceptable hydrate thereof for use in the prevention or treatment of the condition, disease, and/or disorder described above. Yet another aspect of the invention is use of a compound represented by formula (I) according to an aspect of the invention or a pharmaceutically acceptable salt thereof, or a pharmaceutically acceptable hydrate thereof in the manufacture of a medicament for the prevention or treatment of the condition, disease, and/or disorder described above. The condition, disease, and/or disorder are preferably any of cardiovascular diseases, inflammatory diseases, vascular diseases, and renal diseases. A compound represented by formula (I) according to an aspect of the invention or the medicament can be used to prevent or treat the condition, disease, and/or disorder described above to sustainably prevent or treat the condition, disease, and/or disorder.

When a medicament comprising a compound represented by formula (I) according to an aspect of the invention as an active ingredient is administered to a subject, particularly a human patient, the precise dose and number of doses will be determined considering many factors including age and sex of the subject, the precise condition (such as severity) of the condition, disease, and/or disorder to be prevented or treated, and the route of administration. The therapeutically effective dose and number of doses should be ultimately determined by the attending physician. Therefore, the compound represented by formula (I), which is an active ingredient in the medicament according to the aspect, will be administered to the subject in the therapeutically effective dose and number of doses. For example, when the medicament according to the aspect is administered to a human patient, a dose of the compound represented by formula (I), which is an active ingredient, will usually range from 0.01 to 100 mg per 60 kg of body weight per day and typically from 0.01 to 10 mg per 60 kg of body weight per day.

Route of administration and number of doses of a medicament comprising a compound represented by formula (I) according to an aspect of the invention as an active ingredient are not particularly limited and the medicament may be administered orally or parenterally in a single dose or in multiple doses. The medicament according to the aspect is preferably administered parenterally such as intravenously, by intestinal infusion, subcutaneously, intramuscularly, or intraperitoneally, and more preferably intravenously or subcutaneously. The medicament according to the aspect is also preferably administered in a single dose. The medicament according to the aspect is particularly preferably used in intravenous or subcutaneous administration in a single dose. Adrenomedullin, which is the parent molecule of compounds represented by formula (I) according to an aspect of the invention, has a strong vasodilatory effect. This strong vasodilatory effect may cause unwanted side effects such as excessive decreased blood pressure, tachycardia associated with increased reflex sympathetic nerve activity, and/or increased activity of renin when a therapeutically effective amount of adrenomedullin is administered in a single dose. On the other hand, a compound represented by formula (I) according to an aspect of the invention can significantly prolong blood half-life as compared to natural adrenomedullin while retaining adrenomedullin activity substantially approximately equivalent to that of natural adrenomedullin. Therefore, intravenous administration of the medicament comprising a compound represented by formula (I) according to an aspect of the invention as an active ingredient to a subject in a single dose allows the medicament to sustainably prevent or treat a condition, disease, and/or disorder in the subject while suppressing unwanted side effects due to the vasodilation effect of adrenomedullin.

<3. Method for Producing Adrenomedullin Derivatives>

Yet another aspect of the invention relates to a method for producing a compound represented by formula (I) according to an aspect of the invention.

The compound represented by formula (I) according to an aspect of the invention has a protein or polypeptide structure as a whole. Therefore, the compound represented by formula (I) according to an aspect of the invention can be produced on the basis of various means, such as synthesis means or culture means, which are used in the art for synthesizing proteins or polypeptides.

For example, in the case of producing a compound represented by formula (I) according to an aspect of the invention on the basis of culture means, a host cell capable of producing the compound represented by formula (I) according to an aspect of the invention is prepared and subsequently allowed to overexpress the compound of interest. Therefore, the method according to the aspect based on the culture means comprises an expression step of overexpressing the compound represented by formula (I) according to an aspect of the invention in a host cell capable of producing the compound.

The host cell capable of producing the compound represented by formula (I) according to an aspect of the invention can be obtained by obtaining an isolated nucleic acid having a nucleotide sequence encoding the compound represented by formula (I) according to an aspect of the invention, subsequently linking the nucleic acid to a vector, and introducing the resultant to cells such as *Escherichia coli* or *Saccharomyces cerevisiae* for transformation. Therefore, another aspect of the invention relates to an isolated nucleic acid comprising a nucleotide sequence encoding a compound represented by formula (I) according to an aspect of the invention. Yet another aspect of the invention relates to a vector or a host cell comprising a nucleic acid according to an aspect of the invention.

The isolated nucleic acid according to an aspect of the invention preferably has a nucleotide sequence corresponding to various embodiments of the compound represented by formula (I) according to an aspect of the invention described above, and more preferably has a nucleotide sequence selected from the group consisting of SEQ ID NOs: 14, 16, 18, 20, 30, 32, 34, 36, 40, 42, 44 and 46.

The vector and the host cell according to an aspect of the invention can be obtained using various vectors and host cells commonly used in the expression and/or recombination of recombinant genes in the art. Vectors that are used for obtaining the vector according to the aspect can include, for example, plasmid vectors such as pUC119, pUC118 and pGEM T-Easy vectors for gene expression, and plasmid vectors such as pET-11a, pET-3a and pET-32a for protein expression. Cells that are used for obtaining the host cell according to the aspect can include, for example, cells such as *Escherichia coli, Saccharomyces cerevisiae*, and animal cells (such as HEK293 and CHO).

For example, in the case of producing a compound represented by formula (I) according to an aspect of the invention on the basis of synthesis means, a peptide chain having the amino acid sequence of the compound represented by formula (I) according to an aspect of the invention can be synthesized by peptide synthesis on solid phase system or in liquid phase system. Therefore, the method according to the aspect based on the synthesis means comprises a peptide chain synthesis step of synthesizing a peptide chain having the amino acid sequence of the compound represented by formula (I) according to an aspect of the invention by peptide synthesis on solid phase system or in liquid phase system.

In the method according to the aspect based on the synthesis means, a compound represented by formula (I) that has a disulfide bond formed by two cysteine residues in the amino acid sequence can be obtained by disulfide bond formation between thiol groups of two cysteine residues in the amino acid sequence of the peptide chain obtained by the peptide chain synthesis step. Also, a compound represented by formula (I) in which the disulfide bond formed between two cysteine residues in the amino acid sequence of the peptide chain obtained by the peptide chain synthesis step has been substituted with an ethylene group can be obtained by substitution of the disulfide bond with an ethylene group. The formation reaction of a disulfide bond and the substitution reaction with an ethylene group can be performed based on any condition commonly used in the art.

When at least any of the peptide chain obtained by the peptide chain synthesis step and a precursor thereof are in a protected form in the method according to the aspect based on the synthesis means, the method according to the aspect may comprise a protection step in which one or more protecting groups are introduced into the peptide chain or the precursor thereof and/or a deprotection step in which at least any of one or more protecting groups in protected forms of the peptide chain or the precursor thereof are deprotected, as desired. The protection and deprotection steps can be performed with any protection and deprotection reaction commonly used in the art.

EXAMPLES

Hereinafter, the present invention will be described further specifically with reference to Examples. However, the technical scope of the present invention is not intended to be limited by these Examples.

Experiment I: Preparation of Recombinant Gene Encoding Adrenomedullin Derivative Experiment I-1: Design and Analysis of Recombinant Gene Recombinant genes of adrenomedullin derivatives having the structures given below were designed on the basis of the Fc region of immunoglobulin G1 (IgG1), the Fc region of immunoglobulin G4 (IgG4), human adrenomedullin (AM), and the linking groups given below. As for the genes used, identification of restriction enzyme sites in nucleotide sequences, confirmation of the nucleotide sequences, design of primers, and analysis of the amino acid sequences, molecular weights, isoelectric points and the like of corresponding proteins were performed using gene information processing software GENETIX Ver. 13 (Genetyx Corp.).

Example 1: (IgG1 Fc Region)+(Linker S)+(AM-Gly); (SEQ ID NOs: 14 and 15)

Example 2: (IgG1 Fc Region)+(Linker K)+(AM-Gly); (SEQ ID NOs: 16 and 17)

Example 3: (IgG4 Fc Region)+(Linker S)+(AM-Gly); (SEQ ID NOs: 18 and 19)

Example 4: (IgG4 Fc Region)+(Linker K)+(AM-Gly); (SEQ ID NOs: 20 and 21)

Example 5: (IgG1 Fc Region)+(Linker S)+(AM (6-52)-Gly); (SEQ ID NOs: 30 and 31)

Example 6: (IgG1 Fc Region)+(Linker K)+(AM (6-52)-Gly); (SEQ ID NOs: 32 and 33)

Example 7: (IgG1 Fc Region)+(Linker S)+(AM (11-52)-Gly); (SEQ ID NOs: 34 and 35)

Example 8: (IgG1 Fc Region)+(Linker K)+(AM (11-52)-Gly); (SEQ ID NOs: 36 and 37)

Comparative Example 1: (IgG1 Fc Region)+(AM-Gly); (SEQ ID NOs: 38 and 39)

Example 9: (IgG4 Fc Region)+(Linker S)+(AM (6-52)-Gly); (SEQ ID NOs: 40 and 41)

Example 10: (IgG4 Fc Region)+(Linker K)+(AM (6-52)-Gly); (SEQ ID NOs: 42 and 43)

Example 11: (IgG4 Fc Region)+(Linker S)+(AM (11-52)-Gly); (SEQ ID NOs: 44 and 45)

Example 12: (IgG4 Fc Region)+(Linker K)+(AM (11-52)-Gly); (SEQ ID NOs: 46 and 47)

Comparative Example 2: (IgG4 Fc Region)+(AM-Gly); (SEQ ID NOs: 48 and 49)

```
Linker S:
Amino acid sequence:
                                  (SEQ ID NOs: 22)
GGGGSGGGGSGGGGS;

Nucleotide sequence:
                                  (SEQ ID NOs: 23)
GGA GGA GGA GGA TCA GGA GGA GGA

GGA TCA GGA GGA GGA GGA TCA
```

-continued

Linker K:
Amino acid sequence:
(SEQ ID NOs: 24)
GGGGSGGGGSGGGGK

Nucleotide sequence:
(SEQ ID NOs: 25)
GGA GGA GGA GGA TCA GGA GGA GGA

GGA TCA GGA GGA GGA GGA AAG

Experiment I-2: Preparation of DNA Fragment

DNA fragments encoding the Fc region of IgG1, the Fc region IgG4, and human adrenomedullin (AM) were cloned. For the Fc region of IgG1, see the literature of Ellison et al. (Ellison J W, Nucleic Acids Res. 1982; 10 (10); 4071-9) and GenBank: JN222933. For the Fc region of IgG4, see the literature of Labrijn et al. (Labrijn A F, J Immunol. 2011; 187 (6): 3238-46). For AM, see the literature of Kitamura et al. (Kitamura K et al., BBRC. 1993; 194 (2); 720-5). Cloning of each DNA fragment was performed using rTaq (Takara Bio Inc.). PCR was performed under a reaction condition of 94° C. for 2 minutes, and then 30 cycles each involving 94° C. for 30 seconds, 50° C. for 30 seconds, and 72° C. for 1 minute, followed by 72° C. for 10 minutes. The linking group moieties were obtained by synthesizing DNA fragments having the nucleotide sequences described below using a DNA synthesis apparatus.

Experiment I-3: Purification of DNA Fragment

The DNA fragments amplified by PCR were separated by agarose gel electrophoresis. The DNA fragment of interest was excised from the agarose gel and purified using QIAquick Gel Extraction Kit (Qiagen N.V.).

Experiment I-4: Restriction Enzyme Treatment

The purified DNA fragment and vector DNA were treated with restriction enzymes according to the protocol of High-Fidelity (HF) restriction enzyme set (New England BioLabs Inc.). The vector used was a vector pUC119 for gene expression (Takara Bio Inc.) (Novagen).

Experiment I-5: Ligation

The DNA fragment of interest (insert DNA) and 50 ng of the vector DNA treated with restriction enzymes were mixed at the insert DNA: vector molar ratio of 3:1. To this mixed solution, 2× Ligation Mix (Nippon Gene Co., Ltd.) was added in an amount equal to the amount of the mixed solution, and the mixture was reacted at 16° C. for 30 minutes.

Experiment I-6: Transformation

The ligated plasmid DNA was introduced to Escherichia coli for transformation according to the protocol of Escherichia coli for gene expression (HST04 dam-/dcm-Competent Cells (Takara Bio Inc.))

Experiment I-7: Confirmation of Nucleotide Sequence of Recombinant Gene

A recombinant plasmid was purified from the colony of the transformed Escherichia coli using QIAprep Spin Miniprep Kit (Qiagen N.V.). The nucleotide sequence of the purified plasmid was confirmed using Applied Biosystems 3730x1 DNA analyzer (Applied Biosystems, Inc.). As a result, all the recombinant genes of Examples 1 to 12 and Comparative Examples 1 and 2 were confirmed to have the predetermined nucleotide sequence.

Experiment II: Preparation of Adrenomedullin Derivative Protein

Experiment II-1: Design and Analysis of Recombinant Gene

The DNA fragment of interest incorporated in the vector pUC119 for gene expression and a vector pET-11a (Novagen) for protein expression were treated with restriction enzymes Nde I and Bam HI according to the protocol of New England BioLabs Inc. The DNA fragment obtained by the restriction enzyme treatment was separated by agarose gel electrophoresis. The DNA fragment of interest was excised from the agarose gel and purified using QIA quick Gel Extraction Kit (Qiagen N.V.).

Experiment II-2: Ligation

The DNA fragment of interest (insert DNA) and 50 ng of the vector DNA treated with restriction enzymes were mixed at the insert DNA: vector molar ratio of 3:1. To this mixed solution, 2× Ligation Mix (Nippon Gene Co., Ltd.) was added in an amount equal to the amount of the mixed solution, and the mixture was reacted at 16° C. for 30 minutes.

Experiment II-3: Transformation

The ligated plasmid DNA was introduced to Escherichia coli for transformation according to the protocol of Escherichia coli for gene expression from Merck Millipore. The Escherichia coli for gene expression used was BL21 competent cells for the recombinants of the adrenomedullin derivatives of Examples 1, 2 and 5 to 12 and Comparative Examples 1 and 2, and Rosetta competent cells for the recombinants of the adrenomedullin derivatives of Examples 3 and 4.

Experiment II-4: Induction of Expression of Protein of Interest

Escherichia coli confirmed to have the introduced plasmid DNA with the DNA fragment of interest incorporated therein was induced to express the protein of interest using isopropyl-β-thiogalactopyranoside (IPTG). On the day previous to main culture, bacterial cells were extracted with a toothpick from the colony of Escherichia coli cultured in an LB agar medium containing ampicillin and inoculated to an LB liquid medium containing ampicillin. This Escherichia coli inoculated to the LB liquid medium was shake-cultured overnight at 37° C. (preculture). The precultured cell suspension was added in an amount of 10% of the total volume to an LB liquid medium containing ampicillin and shake-cultured at 37° C. (main culture). The main culture was continued until the absorption intensity at 600 nm of the culture solution ranged from 0.5 to 1.0. The absorption intensity reached the predetermined one in 3 hours for the BL21 strain and in 4 hours for the Rosetta strain. IPTG was added at a concentration of 1 mM to the culture solution.

Shake culture was performed at 35° C. for 4 hours and then, bacterial cells were recovered from the culture solution.

Experiment II-5: Recovery of Bacterial Cell

The main culture solution obtained in Experiment II-4 was placed in an amount of 50 mL in a 50 mL tube and centrifuged at 10,000×g at 4° C. for 5 minutes. After removal of the supernatant, additional 50 mL of the culture solution was added to the same tube as above and centrifuged under the same condition as above. After removal of the supernatant, 5 mL of 25 mM Tris-HCl+2.5 mM EDTA+1% NaCl+0.2 mM DTT (pH 7.2) was added to 10 mL of the culture solution to suspend bacterial cells. The suspension was centrifuged at 10,000×g at 4° C. for 5 minutes. After removal of the supernatant, the precipitates of the bacterial cells were frozen overnight at −80° C. The frozen bacterial cells were preserved at −20° C.

Experiment II-6: Homogenization of Bacterial Cell

To the bacterial cells obtained in Experiment II-5, 25 mM Tris-HCl+2.5 mM EDTA+1% NaCl+0.2 mM DTT (pH 7.2) was added in an amount of ⅕ of the amount of the culture solution used for the recovery of the bacterial cells, to suspend bacterial cells. The suspension was centrifuged at 20,000×g at room temperature for 5 minutes. After removal of the supernatant, BugBuster Master Mix (Merck Millipore) was added in an amount of 5 mL per 100 mL of the culture solution used for the recovery of the bacterial cells to the precipitates to suspend bacterial cells. The suspension was shaken at room temperature for 20 minutes and then centrifuged at 16,000×g at 4° C. for 20 minutes. After recovery of the supernatant, 25 mM Tris-HCl+2.5 mM EDTA+0.1% Triton+0.2 mM DTT (pH 7.2) was added in an amount of 1/10 of the amount of the culture solution used for the recovery of the bacterial cells to the precipitates to suspend bacterial cells. The suspension was centrifuged at 20,000×g at room temperature for 5 minutes. Then, the supernatants and the precipitates were separated therebetween and each was preserved.

Experiment 11-7: Confirmation of Protein by SDS-PAGE

Whether the supernatants and precipitates of the homogenized bacterial cells obtained in Experiment 11-6 contained the protein of interest was confirmed by SDS-PAGE based on the laboratory textbook ("PAGE Hajimeteno Denkieido (Introductory Electrophoresis in English) Tanpakushitsu no PAGE (PAGE of proteins in English)" (atto.co.jp/site/download request/experiment), ATTO Corp.). The results of separating the precipitated fraction of the homogenized bacterial cells obtained in Experiment 11-6 by SDS-PAGE are shown in FIG. 1. In the figure, lanes 1 and 6 depict a molecular weight standard, and lanes 2, 3, 4 and 5 depict the precipitated fractions obtained from the recombinants of the adrenomedullin derivatives of Examples 1, 2, 3 and 4. As shown in FIG. 1, the precipitated fractions were confirmed to contain the protein of interest as an inclusion body (in the figure, arrows).

Experiment III: Refolding of Recombinant Protein, and Isolation and Purification Thereof Experiment III-1: Refolding The inclusion body was suspended by the addition of 8 M urea+25 mM Tris-HCl+2.5 mM EDTA+0.2 mM DTT (pH 7.5). Precipitates contained in the suspension were thoroughly dissolved by ultrasonication. The concentration of the dissolved precipitates was adjusted to 200 µg/mL. This solution was placed in Snake Skin™ dialysis tube (Thermo Fisher Scientific Inc.) and dialyzed at 4° C. for 5 hours against 25 mM Tris-HCl+2.5 mM EDTA+0.1 mM GSSG (pH 7.2) as an external dialysis solution. The external solution was replaced with fresh 25 mM Tris-HCl+2.5 mM EDTA+0.1 mM GSSG (pH 7.2) and the solution was further dialyzed overnight at 4° C. Replacement of the external solution was performed once or twice. In this dialysis, an external solution containing arginine may be used. The dialyzed sample was recovered into a tube and centrifuged at 20,000×g at 4° C. for 20 minutes. The supernatant obtained by the centrifugation was used in the subsequent purification.

The amount of a purified refolded product recovered per 400 mL of the culture solution is shown in Table 1 as to Examples 1 to 12. In Comparative Examples 1 and 2, association and precipitation presumably attributed to poor physical properties significantly arose in the refolding step of Experiment III-1, though there was no problem with expression and production in *Escherichia coli*. As a result, the purified product was difficult to obtain in these Comparative Examples.

TABLE 1

| Example | 280 nm absorbance | Amount recovered (mL) |
| --- | --- | --- |
| 1 | 8.4584 | 4.2 |
| 2 | 2.1675 | 24 |
| 3 | 0.3264 | 7.5 |
| 4 | 0.4155 | 4 |
| 5 | 3.1542 | 15 |
| 6 | 0.2753 | 110 |
| 7 | 1.733 | 24 |
| 8 | 2.9474 | 8 |
| 9 | 2.5286 | 4 |
| 10 | 0.3663 | 7.7 |
| 11 | 0.2381 | 5.5 |
| 12 | 0.3645 | 5 |

Experiment III-2: Purification of Refolded Recombinant Protein

The refolded recombinant protein was purified from the supernatant obtained by the centrifugation in Experiment III-1 according to the protocol of HiTrap Protein A HP and Ab Buffer Kit (GE Healthcare Japan Corp.). The purified recombinant protein was diluted with a 20 mM citrate buffer (pH 7.2). The concentration of the dilution and replacement of the solvent were conducted by using Amicon Ultra-15 Ultracel-10K (Merck Millipore).

Experiment III-3: Confirmation of Amino Acid Sequence of Recombinant Protein with Protein Sequencer The refolded recombinant proteins of Examples 1, 2, 3, 4 and 5 obtained in Experiment III-2 were separated by SDS-PAGE. The SDS-PAGE gel was transferred to a polyvinylidene fluoride (PVDF) membrane using EzBlot (ATTO Corp.). The N-terminal amino sequences of the recombinant proteins of Examples 1, 2, 3, 4 and 5 contained in the samples transferred to the PVDF membrane were confirmed using a protein sequencer (Examples 1 to 4: Procise 494 HT Protein Sequencing System, Applied Biosystems, Inc.; Example 5: PPSQ-33A, Shimadzu Corp.). As a result, the recombinant proteins of Examples 1, 2 and 5 were confirmed to have an amino acid sequence identical to the N-terminal amino acid sequence of IgG1, and the recombinant proteins of Examples 3 and 4 were confirmed to have an amino acid sequence identical to the N-terminal amino acid sequence of IgG4.

Experiment III-4: Amidation of Recombinant Protein

To 130 µg of the recombinant protein of Example 1, 4 mM ascorbic acid, 10 µM $CuSO_4$, 100 µg/mL catalase, and 500 ng/mL amidating enzyme (Recombinant Human Peptidylglycine α-Amidating Monooxygenase/PAM, R&D Systems Inc.) were added, and the total amount of the mixture was adjusted to 200 µL with a 50 mM sodium acetate solution (pH 5.5). The reaction solution was reacted overnight at 37° C. Then, the reaction was terminated by adding 20 µL of 250 mM EDTA to the reaction solution. Amidation of the recombinant protein was confirmed by the IRMA method (Ohta H, Tsuji T, Asai S et al., One-step direct assay for mature-type adrenomedullin with monoclonal antibodies. Clin Chem, Vol. 45, p. 244-251, 1999) using an antibody recognizing the amidated C-terminus of adrenomedullin.

Experiment IV: Use Examples of Adrenomedullin Derivative—(1)

Experiment IV-1: Intracellular cAMP Concentration-Increasing Effect of Adrenomedullin Derivative The physiological effect of AM is known to be exerted via increase in the concentration of intracellular cAMP (see Non Patent Literature 1). Accordingly, the adrenomedullin derivative of each Example was added to a cultured cell line (HEK293 cell line) caused to express an AM receptor, and the amount of intracellular cAMP produced was measured. $10^{-7}$ mol/L of the adrenomedullin derivative of Example 1 or 2, or adrenomedullin-glycine (AM-Gly) was added to confluent HEK293 cells in the presence of 0.5 mM IBMX and incubated for 15 minutes. Then, the intracellular cAMP concentration in the HEK293 cells of each test sample was measured using an ELISA kit for cAMP measurement (GE Healthcare Japan Corp., #RPN2251). As a result, both the tested adrenomedullin derivatives of Examples 1 and 2 exhibited increasing effects on intracellular cAMP concentration at the same level as in AM-Gly. Therefore, the adrenomedullin derivatives having the linked Fc region of an immunoglobulin are presumed to maintain bioactivity at the same level as in the parent compound AM-Gly.

Experiment IV-2: Increasing Effect of Amidated Adrenomedullin Derivative on Intracellular cAMP Concentration Any one of the amidated compounds of Examples 1 to 12 and human AM (hAM) were added to a cultured cell line (HEK293 cell line) caused to express an AM receptor, and incubated for 15 minutes. The other procedures were performed by the same procedures as in Experiment IV-1. When the largest activity obtained by the addition of hAM was defined as 100%, the results about the compounds of Examples 1 to 12 added at $10^{-6}$ M were calculated as relative values. The results are shown in Table 2.

TABLE 2

| Example | Relative activity (%) (vs. hAM) |
|---------|---------------------------------|
| 1 | 27 |
| 2 | 11 |
| 3 | 27 |
| 4 | 49 |
| 5 | 88 |
| 6 | 70 |
| 7 | 68 |
| 8 | 48 |
| 9 | 54 |
| 10 | 39 |
| 11 | 36 |
| 12 | 48 |

As shown in Table 2, the Fc fusion protein with N-terminally deleted AM was confirmed to have a tendency of relatively high activity as compared to the Fc fusion protein with the full-length AM, i.e., hAM. Particularly, the fusion proteins with the IgG1 Fc region of Examples 5 to 8 exhibited significantly high activity.

Experiment IV-3: Time Course of Concentration in Blood of Subcutaneously Administered Adrenomedullin Derivative A physiological saline solution of 10 nmol/kg compound of Example 1 (hereinafter, also simply referred to as "Example 1") or compound of Example 5 (hereinafter, also simply referred to as "Example 5") was subcutaneously administered to each 7-week-old Wistar rat (approximately 300 g). Inhalation anesthesia was performed with isoflurane before the administration (0) and 60 minutes, 160 minutes, 8 hours, 1 day, and 2 days after the administration. Under anesthesia, 200 µL of blood was collected from the vein under the collarbone in a state supplemented with EDTA-2Na and aprotinin. The obtained blood was centrifuged at 3,000 rpm for 10 minutes to obtain plasma. The concentration of AM in the plasma was measured by the IRMA method. Time course of the concentration in blood of the subcutaneously administered AM derivative of Example 1 or 5 is shown in FIG. 2.

Figure 2:
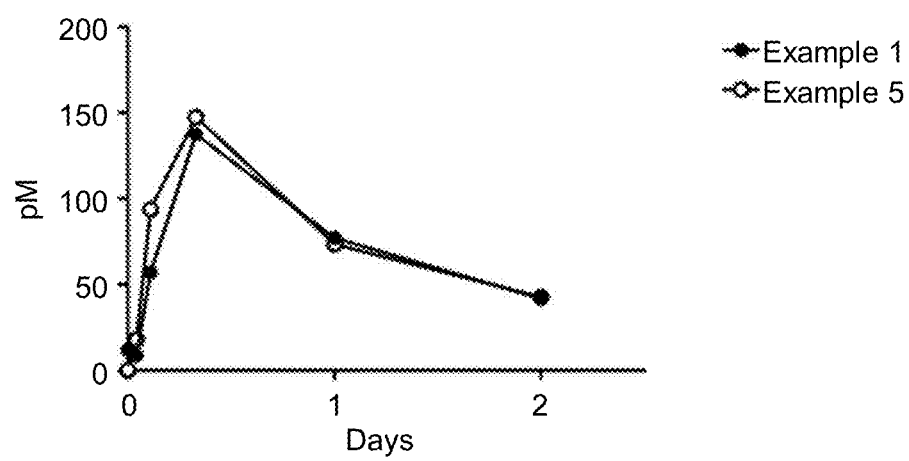
FIG. 2 shows time course of the concentrations in blood of subcutaneously administered adrenomedullin derivatives of Examples 1 or 5.

As shown in FIG. 2, a therapeutically sufficient amount of the AM derivative was present in the blood even 2 days after the administration when Example 1 or 5 was subcutaneously administered.

Experiment IV-4: Time Course of Concentration in Blood of Adrenomedullin Derivative Administered from Tail Vein A physiological saline solution of 10 nmol/kg Example 1 or 5 was administered to each 7-week-old Wistar rat (approximately 300 g) from the tail vein. Inhalation anesthesia was performed with isoflurane before the administration (0) and 2 days after the administration. Under anesthesia, 200 µL of blood was collected from the vein under the collarbone in a state supplemented with EDTA-2Na and aprotinin. The obtained blood was centrifuged at 3,000 rpm for 10 minutes to obtain plasma. The concentration of AM in the plasma was measured by the IRMA method. The concentration in blood of the AM derivative of Example 1 or 5 administered from the tail vein 2 days after the administration is shown in FIG. 3.

Figure 3:
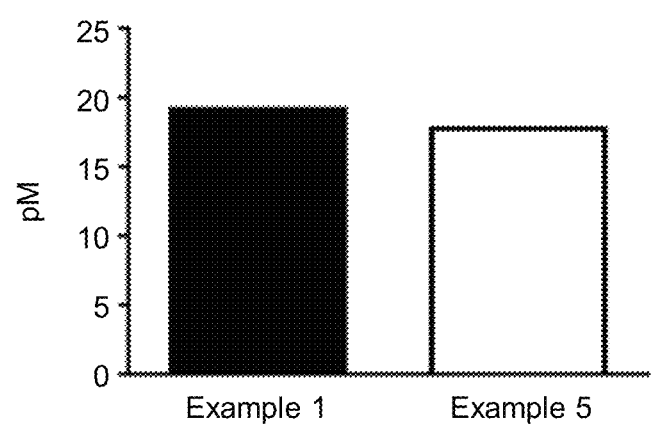
FIG. 3 shows the concentrations in blood of adrenomedullin derivatives of Examples 1 or 5 administered from the tail vein, 2 days after the administration of the adrenomedullin derivatives.

As shown in FIG. 3, a therapeutically sufficient amount of the AM derivative was present in the blood even 2 days after the administration when Example 1 or 5 was administered from the tail vein.

Experiment V: Use Examples of Adrenomedullin Derivative—(2)

Experiment V-1: Suppressing Effect of Adrenomedullin Derivative on Blood Pressure Increase on Spontaneously Hypertensive Rat (SHR)

Figure 4:
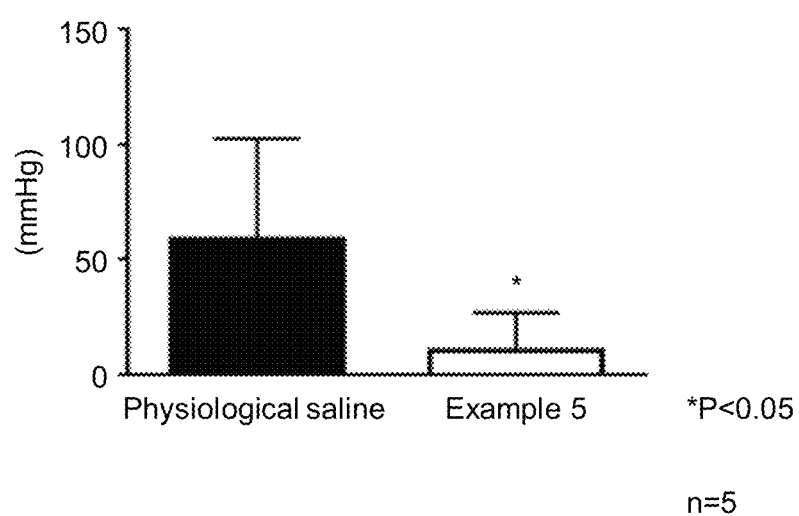
FIG. 4 shows suppressing effect of a subcutaneously administered adrenomedullin derivative of Example 5 on the blood pressure increase on spontaneously hypertensive rats (SHR). In the figure, the ordinate depicts a difference in blood pressure (mmHg) obtained by subtracting systolic blood pressure before the administration from systolic blood pressure 9 days after the administration. * depicts a p value of less than 0.05 vs. a control group (physiological saline administration group) calculated by the Student's t-test (n=5).

Example 5 was studied for its suppressing effect of subcutaneous administration according to the following procedures on blood pressure increase on SHR. A physiological saline solution of 50 nmol/kg Example 5 was subcutaneously administered in a single dose to each 8-week-old SHR fed with a high-salt diet. The same amount as above of physiological saline was subcutaneously administered in a single dose as a control group. Blood pressure was measured before the administration and 9 days after the administration in a tail cuff. Blood was collected at the completion of the experiment (10 days after the administration) and the concentration in blood of Example 5 was measured. The suppressing effect of subcutaneously administered Example 5 on blood pressure increase on SHR is shown in FIG. 4. In the figure, the ordinate depicts a difference in blood pressure (mmHg) obtained by subtracting systolic blood pressure before the administration from systolic blood pressure 9 days after the administration. * depicts a p value of less than 0.05 vs. the control group (physiological saline administration group) calculated by the Student's t-test (n=5).

As shown in FIG. 4, increase in blood pressure was significantly suppressed in the Example 5 administration group as compared to the control group (physiological saline administration group). Also, Example 5 was present in blood even 10 days after the administration (data not shown).

Figure 5:
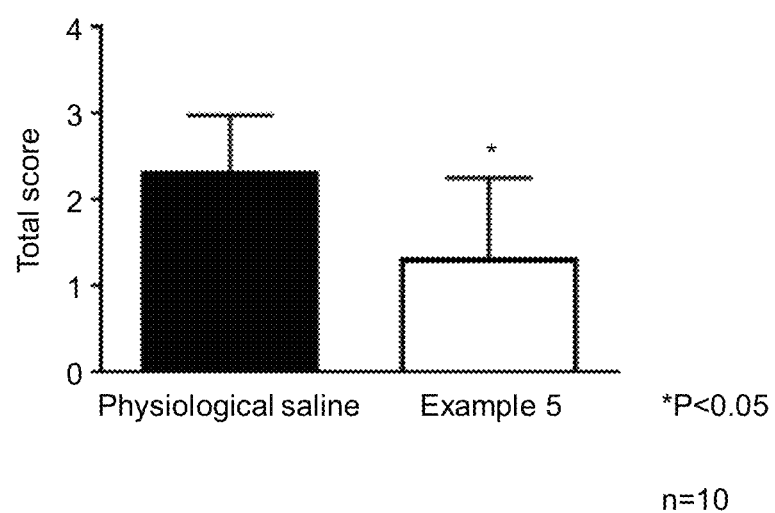
FIG. 5 shows improving effect of a subcutaneously administered adrenomedullin derivative of Example 5 on the inflammation on dextran sodium sulfate (DSS)-induced colitis model mice. In the figure, the ordinate depicts total score on day 5 in a control group or an administration group of the adrenomedullin derivative of Example 5. * depicts a p value of less than 0.05 vs. the control group (physiological saline administration group) calculated by the Student's t-test (n=10).

Experiment V-2: Pharmacological Effect on Dextran Sodium Sulfate (DSS)-Induced Colitis Model Example 5 was studied for its inflammation-improving effect on mouse DSS-induced colitis models by subcutaneous administration according to the following procedures. A physiological saline solution of 50 nmol/kg Example 5 was subcutaneously administered to the back of each mouse. The same amount as above of physiological saline was subcutaneously administered in a single dose as a control group. On the day following the administration, colitis model preparation was started by administration of 3% DSS as drinking water for 5 days (this day was defined as day 0). The body weight and the form of stool were observed on days 0, 3 and 5 and evaluated on the basis of the scores shown in Table 3. The intestinal tract was collected on the final day and its wet weight was compared between the groups. The inflammation-improving effect of subcutaneously administered Example 5 on the DSS-induced colitis model mice is shown in FIG. 5. In the figure, the ordinate depicts total score on day 5 in the control group or the Example 5 administration group. * depicts a p value of less than 0.05 vs. the control group (physiological saline administration group) calculated by the Student's t-test (n=10).

TABLE 3

|  | Criteria |
|---|---|
| Weight loss | |
| 0 | No weight loss |
| 1 | 1-5% |
| 2 | 5-10% |
| 3 | 10-20% |
| Stool consistency | |
| 0 | Normal |
| 2 | Loose stool |
| 4 | Diarrhea |
| Bleeding/mucous and bloody stool | |
| 0 | Normal |
| 2 | Bleeding |
| 4 | Mucous and bloody stool |

As shown in FIG. 5, the inflammation score was significantly alleviated in the Example 5 administration group as compared to the control group (physiological saline administration group) on day 5. Also, the wet weight of the intestinal tract was significantly smaller in the Example 5 administration group as compared to the control group (physiological saline administration group) (data not shown). These results suggest that the administration of Example 5 alleviates inflammation in the large intestine.

All publications, patent and patent applications cited herein are incorporated herein by reference in their entirety.

The invention claimed is:

1. A compound represented by formula (I), a salt thereof, or a hydrate thereof:

A-L-B    (I)

wherein
A is an Fc region of an immunoglobulin G1 (IgG1) or an Fc region of immunoglobulin G4 (IgG4),
B is a peptide moiety derived from following peptide (i), (ii) or (iii):
(i) a peptide consisting of an amino acid sequence of an adrenomedullin,
(ii) a peptide that consists of an amino acid sequence of an adrenomedullin and has a disulfide bond formed by two cysteine residues in the amino acid sequence, and
(iii) peptide of (i) or (ii) wherein the peptide has deletion of amino acid residues at positions between one and fifteen from the N-terminus thereof,
wherein each of the peptides (i), (ii) and (iii) is amidated at the C-terminus thereof and/or has a glycine residue added to the C-terminus thereof,
and
L is a linking group comprising a peptide having the following amino acid sequence:
(GGGGS)n (SEQ ID NO:27); or
a sequence consisting of (GGGGS)n (SEQ ID NO:27) and GGGGK (SEQ ID NO:29),
wherein n is an integer from 2 to 6;
wherein the Fc region A is linked to the linking group L through a peptide bond formed by the C-terminal carboxyl group of the Fc region A and the N-terminal a-amino group of the linking group L, and
the peptide moiety B is linked to the linking group L through a peptide bond formed by the N-terminal a-amino group of the peptide moiety B and the C-terminal carboxyl group of the linking group L.

2. The compound, the salt thereof, or the hydrate thereof according to claim 1, wherein L is a linking group comprising a peptide having the following amino acid sequence:

GGGGSGGGGSGGGGS;    (SEQ ID NO: 22)
or
GGGGSGGGGSGGGGK,    (SEQ ID NO: 24)

3. The compound, the salt thereof, or the hydrate thereof according to claim 1, wherein B comprises peptide (iv) or (v):
(iv) the peptide of (i) or (ii) wherein the peptide is amidated at the C-terminus thereof, and
(v) the peptide of (i) or (ii) wherein the peptide has a glycine residue added to the C-terminus thereof.

4. The compound, the salt thereof, or the hydrate thereof according to claim 1, wherein B comprises a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of the SEQ ID NO: 4, or a peptide consisting of the amino acid sequence of the SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(g) any peptide of (a) to (f) wherein the peptide has deletion of amino acid residues at positions between 1 and 15 from the N-terminus thereof, wherein each of the peptides (a)-(g) is amidated at the C-terminus thereof and/or has a glycine residue added to the C-terminus thereof.

5. The compound, the salt thereof, or the hydrate thereof according to claim 4, wherein B comprises a peptide selected from the group consisting:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 4, or a peptide consisting of the amino acid sequence of SEQ ID NO: 4 and having a disulfide bond formed by the cysteine residues at positions 16 and 21;
(c) a peptide consisting of the amino acid sequence of SEQ ID NO: 6, or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8, or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10, or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12, or a peptide consisting of the amino acid sequence of SEQ ID NO: 12 and having a disulfide bond formed by the cysteine residues at positions 14 and 19;
(i) any peptide of (a) to (f) wherein the peptide is amidated at the C-terminus thereof; and
(j) any peptide of (a) to (f) wherein the peptide has a glycine residue added to the C-terminus thereof.

6. The compound, the salt thereof, or the hydrate thereof according to claim 1, wherein the compound represented by formula (I) comprises a peptide selected from the group consisting of:

(E-a-1) a peptide consisting of the amino acid sequence of SEQ ID NO: 15, or a peptide consisting of the amino acid sequence of SEQ ID NO: 15 and having a disulfide bond formed by the cysteine residues at positions 259 and 264;
(E-a-2) a peptide consisting of the amino acid sequence of SEQ ID NO: 17, or a peptide consisting of the amino acid sequence of SEQ ID NO: 17 and having a disulfide bond formed by the cysteine residues at positions 259 and 264;
(E-a-3) a peptide consisting of the amino acid sequence of SEQ ID NO: 19, or a peptide consisting of the amino acid sequence of SEQ ID NO: 19 and having a disulfide bond formed by the cysteine residues at positions 256 and 261;
(E-a-4) a peptide consisting of the amino acid sequence of SEQ ID NO: 21, or a peptide consisting of the amino acid sequence of SEQ ID NO: 21 and having a disulfide bond formed by the cysteine residues at positions 256 and 261;
(E-a-5) a peptide consisting of the amino acid sequence of SEQ ID NO: 31, or a peptide consisting of the amino acid sequence of SEQ ID NO: 31 and having a disulfide bond formed by the cysteine residues at positions 254 and 259;
(E-a-6) a peptide consisting of the amino acid sequence of SEQ ID NO: 33, or a peptide consisting of the amino acid sequence of SEQ ID NO: 33 and having a disulfide bond formed by the cysteine residues at positions 254 and 259;
(E-a-7) a peptide consisting of the amino acid sequence of SEQ ID NO: 35, or a peptide consisting of the amino acid sequence of SEQ ID NO: 35 and having a disulfide bond formed by the cysteine residues at positions 249 and 254;
(E-a-8) a peptide consisting of the amino acid sequence of SEQ ID NO: 37, or a peptide consisting of the amino acid sequence of SEQ ID NO: 37 and having a disulfide bond formed by the cysteine residues at positions 249 and 254;
(E-a-9) a peptide consisting of the amino acid sequence of SEQ ID NO: 41, or a peptide consisting of the amino acid sequence of SEQ ID NO: 41 and having a disulfide bond formed by the cysteine residues at positions 251 and 256;
(E-a-10) a peptide consisting of the amino acid sequence of SEQ ID NO: 43, or a peptide consisting of the amino acid sequence of SEQ ID NO: 43 and having a disulfide bond formed by the cysteine residues at positions 251 and 256;
(E-a-11) a peptide consisting of the amino acid sequence of SEQ ID NO: 45, or a peptide consisting of the amino acid sequence of SEQ ID NO: 45 and having a disulfide bond formed by the cysteine residues at positions 246 and 251;
(E-a-12) a peptide consisting of the amino acid sequence of SEQ ID NO: 47, or a peptide consisting of the amino acid sequence of SEQ ID NO: 47 and having a disulfide bond formed by the cysteine residues at positions 246 and 251;
(E-g) any peptide of (E-a-1) to (E-a-12) wherein the disulfide bond of the peptide is substituted with an ethylene group;
(E-h) any peptide of (E-a-1) to (E-g) wherein the peptide has the amino acid sequence comprising deletion, substitution, or addition of one to fifteen amino acid residues;
(E-i) any peptide of (E-a-1) to (E-h) wherein the peptide is amidated at the C-terminus thereof; and
(E-j) any peptide of (E-a-1) to (E-h) wherein the peptide has a glycine residue added to the C-terminus thereof.

7. The compound, the salt thereof, or the hydrate thereof according to claim 6, wherein the compound represented by formula (I) comprises a peptide selected from the group consisting of:
(E-a-1) a peptide consisting of the amino acid sequence of SEQ ID NO: 15, or a peptide consisting of the amino acid sequence of SEQ ID NO: 15 and having a disulfide bond formed by the cysteine residues at positions 259 and 264;
(E-a-2) a peptide consisting of the amino acid sequence of SEQ ID NO: 17, or a peptide consisting of the amino acid sequence of SEQ ID NO: 17 and having a disulfide bond formed by the cysteine residues at positions 259 and 264;
(E-a-3) a peptide consisting of the amino acid sequence of SEQ ID NO: 19, or a peptide consisting of the amino acid sequence of SEQ ID NO: 19 and having a disulfide bond formed by the cysteine residues at positions 256 and 261;
(E-a-4) a peptide consisting of the amino acid sequence of SEQ ID NO: 21, or a peptide consisting of the amino acid sequence of SEQ ID NO: 21 and having a disulfide bond formed by the cysteine residues at positions 256 and 261;
(E-a-5) a peptide consisting of the amino acid sequence of SEQ ID NO: 31, or a peptide consisting of the amino acid sequence of SEQ ID NO: 31 and having a disulfide bond formed by the cysteine residues at positions 254 and 259;
(E-a-6) a peptide consisting of the amino acid sequence of SEQ ID NO: 33, or a peptide consisting of the amino acid sequence of SEQ ID NO: 33 and having a disulfide bond formed by the cysteine residues at positions 254 and 259;
(E-a-7) a peptide consisting of the amino acid sequence of SEQ ID NO: 35, or a peptide consisting of the amino acid sequence of SEQ ID NO: 35 and having a disulfide bond formed by the cysteine residues at positions 249 and 254;
(E-a-8) a peptide consisting of the amino acid sequence of SEQ ID NO: 37, or a peptide consisting of the amino acid sequence of SEQ ID NO: 37 and having a disulfide bond formed by the cysteine residues at positions 249 and 254;
(E-a-9) a peptide consisting of the amino acid sequence of SEQ ID NO: 41, or a peptide consisting of the amino acid sequence of SEQ ID NO: 41 and having a disulfide bond formed by the cysteine residues at positions 251 and 256;
(E-a-10) a peptide consisting of the amino acid sequence of SEQ ID NO: 43, or a peptide consisting of the amino acid sequence of SEQ ID NO: 43 and having a disulfide bond formed by the cysteine residues at positions 251 and 256;
(E-a-11) a peptide consisting of the amino acid sequence of SEQ ID NO: 45, or a peptide consisting of the amino acid sequence of SEQ ID NO: 45 and having a disulfide bond formed by the cysteine residues at positions 246 and 251;
(E-a-12) a peptide consisting of the amino acid sequence of SEQ ID NO: 47, or a peptide consisting of the amino acid sequence of SEQ ID NO: 47 and having a disulfide bond formed by the cysteine residues at positions 246 and 251; and (E-i) any peptide of (E-a-1) to (E-a-12) wherein the peptide is amidated at the C-terminus thereof.

8. A composition comprising the compound, the salt thereof, or the hydrate thereof according to claim 1 and one or more pharmaceutically acceptable carriers.

9. The composition according to claim 8 for use in the prevention or treatment of a cardiovascular disease, an inflammatory disease, a vascular disease, or a renal disease.

10. The compound, the salt thereof, or the hydrate thereof according to claim 1, wherein B is the peptide moiety derived from the peptide (iii) of (i) or (ii) wherein the peptide has deletion of amino acid residues at positions between one and fifteen from the N-terminus thereof, wherein the peptide (iii) is amidated at the C-terminus thereof and/or has a glycine residue added to the C-terminus thereof.

* * * * *